US007524646B2

(12) United States Patent
Doring et al.

(10) Patent No.: US 7,524,646 B2
(45) Date of Patent: Apr. 28, 2009

(54) METHOD FOR DIVERSIFYING THE CHEMICAL COMPOSITION OF PROTEINS PRODUCED IN VIVO BY GENETICALLY DISABLING THE EDITING FUNCTION OF THEIR AMINOACYL TRNA SYNTHETASES

(75) Inventors: Volker Doring, Paris (FR); Leslie A. Nangle, San Diego, CA (US); Tamara L. Hendrickson, Baltimore, MD (US); Valerie De Crecy-Lagard, La Jolla, CA (US); Paul Schimmel, La Jolla, CA (US); Philippe Marliere, Etiolles (FR)

(73) Assignees: Institut Pasteur, Paris (FR); The Scripps Research Institute, La Jolla, CA (US); Evologic GmbH, Cologne (DE)

(*) Notice: Subject to any disclaimer, the term of this patent is extended or adjusted under 35 U.S.C. 154(b) by 0 days.

(21) Appl. No.: 11/054,192

(22) Filed: Feb. 8, 2005

(65) Prior Publication Data

US 2005/0170460 A1     Aug. 4, 2005

Related U.S. Application Data

(63) Continuation of application No. 10/126,448, filed on Apr. 19, 2002, now abandoned.

(60) Provisional application No. 60/285,495, filed on Apr. 19, 2001.

(51) Int. Cl.
C12P 21/06 (2006.01)
C12N 9/10 (2006.01)
C12N 9/12 (2006.01)

(52) U.S. Cl. ............... 435/69.1; 435/193; 435/91.4; 435/252.3; 435/252.33; 435/254.11; 435/254.2; 435/325

(58) Field of Classification Search ................. None
See application file for complete search history.

(56) References Cited

U.S. PATENT DOCUMENTS

| 5,370,995 A * | 12/1994 | Hennecke et al. .......... 435/69.1 |
| 2003/0148422 A1 | 8/2003 | Doring et al. |
| 2004/0014942 A1 | 1/2004 | Marliere et al. |

FOREIGN PATENT DOCUMENTS

| AU | 769879 | 5/2000 |
| WO | WO 00/24922 | 5/2000 |
| WO | WO 01/83718 | 11/2001 |

OTHER PUBLICATIONS

Budista et al. Towards the experimental codon reassignment in vivo: protein building with an expanded amino acid repertoire. 1999, FASEB vol. 13, pp. 41-51.*

Ansaldi, et al. "Site-Specific Mutagenesis by Using an Accurate Recombinant Polymerase Chain Reaction Method," Anal. Biochem., (1996) vol. 234: 110-111.
Baldwin, et al. "Transfer Ribonucleic Acid-induced Hydrolysis of Valyadenylate Bound to Isoleucyl Ribonucleic Acid Synthetase*," J. Biol. Chem., (1966) vol. 241: 839-845.
Belfort, et al. "Primary Structure of the Escherichia coli thyA. Gene and Its Thymidylate," Proc. Natl. Acad. Sci. USA, (1983) vol. 80: 4914-4918.
Böck, et al. "Selenocysteine: the $21^{st}$ Amino Acid", Mol. Microbiol., (1991) vol. 5: 515-520.
Brunner J. "Biosynthetic incorporation of non-natural amino acids into proteins", Chemical Society Reviews, Chemical Society, London, GB, 1993, vol. 22, No. 3, 183-189.
Dev, et al. . "Functional Role of Cysteine-146 in Escherichia coli Thymidylate Synthase," Proc. Natl. Acad. Sci. USA, (1988) vol. 85: 1472-1476.
Döring, et al. "Reassigning Cysteine in the Genetic Code of Esherichia coli," Genetics, (1998) vol. 150: 543-551.
Doring, et al. "Enlarging the amino acid set of Escherichia coli by infiltration of the valine coding pathway", Science, 2001, vol. 292, No. 5516, 501-504.
De Felice, et al., "Growth Inhibition of Escherichia coli K-12 by L-Valine: A Consequence of a Regulatory Pattern," Molec. Gen. Genet. 156, 1-7 (1977).
Eldred, et al. "Rapid Deacylation by Isoleucyl Transfer Ribonucleic Acid Synthetase of Isoleucine-specific Transfer Ribonucleic Acid Aminoacylated with Valine," J. Biol. Chem., (1972) vol. 247: 2961-2964.
Fersht. In Structure and Mechanism in Protein Science, (1999) pp. 389-399, Freeman, N.Y.
Fotheringham, et al. "Engineering of a Novel Biochemical Pathway for the Biosynthesis of L-2-aminobutyric Acid in Esherichia coli K12," Biorg. Med. Chem., (1999) vol. 7: 2209-2213.
Gevaert, et al. "Protein Identification Methods in Proteomics," Electrophoresis, (2000) vol. 21: 1145-1154.
Guzman, et al. "Tight Regulation, Modulation, and High-level Expression by Vectors Containing the Arabinose PBAD Promoter", J. Bacteriol., (1995) vol. 177: 4121-4130.
Hendrickson, et al. "Errors from Selective Disruption of the Editing Center in a Trna synthetase", Biochemistry, (2000) vol. 39: 8180-8186.
Hendrickson, et al. "Mutational Separation of Two Pathways for Editing By a Cass Trna Synthetase", Mol. Cell., (2002) vol. 9: 353-362.

(Continued)

Primary Examiner—Rebecca E. Prouty
Assistant Examiner—Kagnew H Gebreyesus
(74) Attorney, Agent, or Firm—Michael B. Rubin; Bozicevic, Field & Francis, LLP

(57) ABSTRACT

The present invention is directed to a method to diversify the chemical composition of proteins produced in vivo comprising the step of disabling, particularly by mutagenesis, the editing function of one of its aminoacyl tRNA synthetases. The present invention is also directed to nucleic acid sequences encoding such mutated aminoacyl tRNA synthetases having their editing site mutated and capable of mischarging its cognate tRNA with a noncanonical amino acid. Also described herein is an improved method for obtaining transformed cells capable of synthetizing in vivo proteins comprising at least a noncanonical amino acid and their use for the production of such proteins.

14 Claims, 7 Drawing Sheets

OTHER PUBLICATIONS

Ibba, et al. "*Aminoacyl-$_T$ RNA Synthesis*," Annu. Rev. Biochem., (2000) vol. 69: 617-650.

Ibba, et al. "Towards engineering proteins by site-directed incorporation in vivo of non-natural amino acids", Bio/Technology, Nature publishing Co. New York, vol. 12, No. 7, 1994, 678-682.

Jakubowski, et al. "*Alternative Pathways for Editing No-Cognate Amino Acids by aminocyl-Trna synthetases*," J. Mol. Biol., (1993) vol. 231: 161-166.

Lemeignan, et al. Phenotypic Suppression by Incorporation of an Alien Amino Acid: *J. Mol. Biol.*, (1993) vol. 231: 161-166.

Lin, et al. "Mutational Analysis Suggests the Same Design for Editing Activities of Two Trna Synthetases+," *Biochemistry*, (1996) vol. 35: 5596-5601.

Lin, et al. "*Dwarf Mice and the Ageing Process*," Nature, (1996) vol. 384: 33-34.

Liu, et al. "Process Toward the Evolution of an Organism with an Expanded Genetic Code," *Proc. Natl. Acad. Sci. USA*, (1999) vol. 96: 4780-4785.

Loftfield, et al. "The Frequency of Errors in Protein Biosynthesis," *J. Biochem J.*, (1972) vol. 128: 1353-1356.

Modrich, et al. "Mechanisms And Biological Effects of Mismatch Repair," *Annu. Rev. Genet.*, (1991) vol. 25: 229-253.

Musier-Forsyth, et al. "Role of Zinc in Translation Accuracy Becomes Crystal Clear," *Nat. Struct. Biol*, (2000) vol. 7: 435-436.

Mursinna, et al. "A conserved threonine wthin *Escherichia coli* leucyl-tRNA synthetase prevents hydrolytic editing of leucyltRNA", Biochemistry (Apr. 11, 2001) 40:5376-5381.

Nureki, et al. "Enzyme Structure with Two Catalytic Sites for Double-Sieve Selection of Substrate," *Science*, (1998) vol. 280: 578-582.

Pine. "Comparative Physiological Effects of Incorporated Amino Acid Analogs In *Esherichia coli*," *Antimicrobio. Agents Chemother.*, (1978) vol. 13: 676-685.

Rajbhandary. "Initiator Transfer RNAs," *J. Bacteriol.*, (1994) vol. 176: 547-552.

Richaud, et al. "Recruitment of Cysteine Thioethers For Constructing The Cell Way of *Escherichia*," *J. Biol. Chem.*, (1993) vol. 268: 26827-26835.

Schmidt, et al. "Mutational Isolation of a Sieve for Editing in a Transfer RNA Synthetase", *Science*, (1994) vol. 264: 265-267.

Schmidt, et al. "Residues in a Class I tRNA Synthetase Which Determine Selectivity of Amino Acid Recognition in the Context of tRNA," *Biochemistry*, (1995) vol. 34: 11204-11210.

Shepard, et al. "RNA binding determinant in some class I TRNA synthetases identified by alignment-guided mutagenesis," *Proc. Natl. Acad. Sci. USA*, (1992) vol. 89: 9964-9968.

Sussman, et al. "Peptide Transport and Metabolism In Bacteria," *Annu. Rev. Biochem.*, (1971) vol. 40: 397-408.

Weber, et al., entitled "Reasons for the Occurrence of the Twenty Coded Protein Amino Acids," J. Mol Evol (1981) 17:273-284.

* cited by examiner

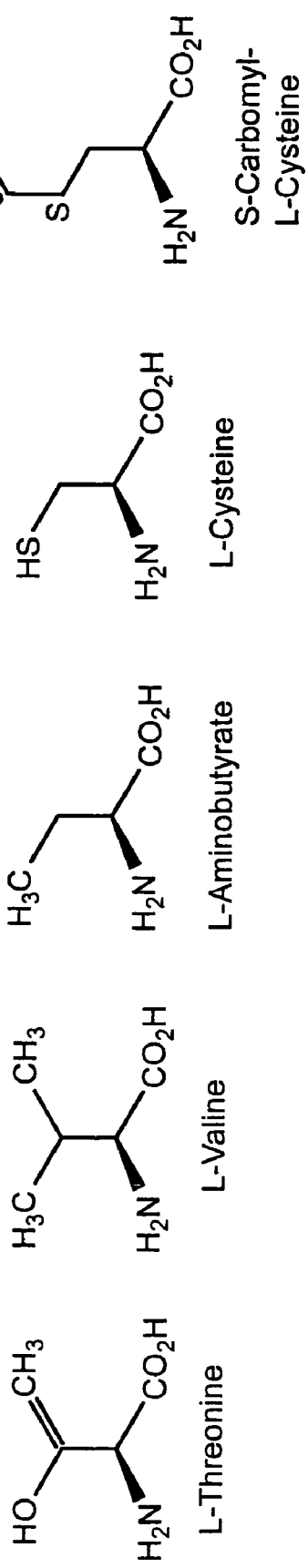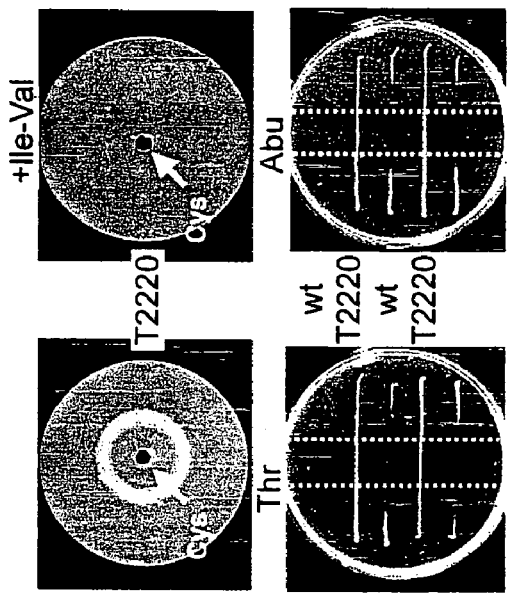
FIG. 1A
FIG. 1B
FIG. 1C

FIG. 2A

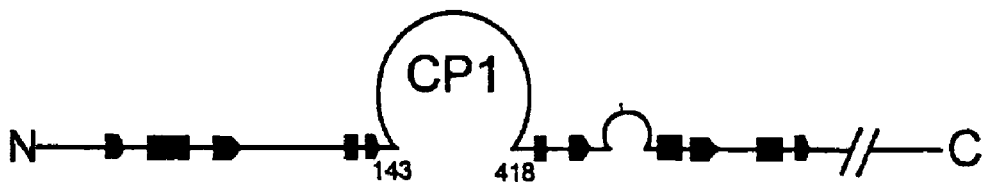

|  |  | 240 | 330 |
|---|---|---|---|
|  | Ec | WTTTPWTLPANRA...GTGAVHTAPGHGPDDY |  |
|  |  | (SEQ ID NO:7) | (SEQ ID NO:8) |
| IleRS | Sc | WTTTPWTLPSNLS...GTGIVHNAPAFGEEDN |  |
|  |  | (SEQ ID NO:9) | (SEQ ID NO:10) |
|  | Hs | WTTTPWTLPSNLA...GTGVVHQAPYFGAEDY |  |
|  |  | (SEQ ID NO:11) | (SEQ ID NO:12) |

\*\*\*\*\*\*\* \* \*\*\* \*\* \* \* \*

|  |  | 220 | 276 |
|---|---|---|---|
|  | Ec | ATTRPETLLGDTG...GTGCVKITPAHDFNDY |  |
|  |  | (SEQ ID NO:13) | (SEQ ID NO:14) |
| ValRS | Sc | ATTRPETIFGDTA...GTGAVKITPAHDQNDY |  |
|  |  | (SEQ ID NO:15) | (SEQ ID NO:16) |
|  | Hs | ATTRIETMLGDVA...GTGAVKITPAHDQNDY |  |
|  |  | (SEQ ID NO:17) | (SEQ ID NO:18) |

\*\*\*\* \*\* \* \*\* \*\* \*
PH N AQ

K P <u>V</u> L E P S D Y F N Y I E L N R (SEQ ID NO: 19)

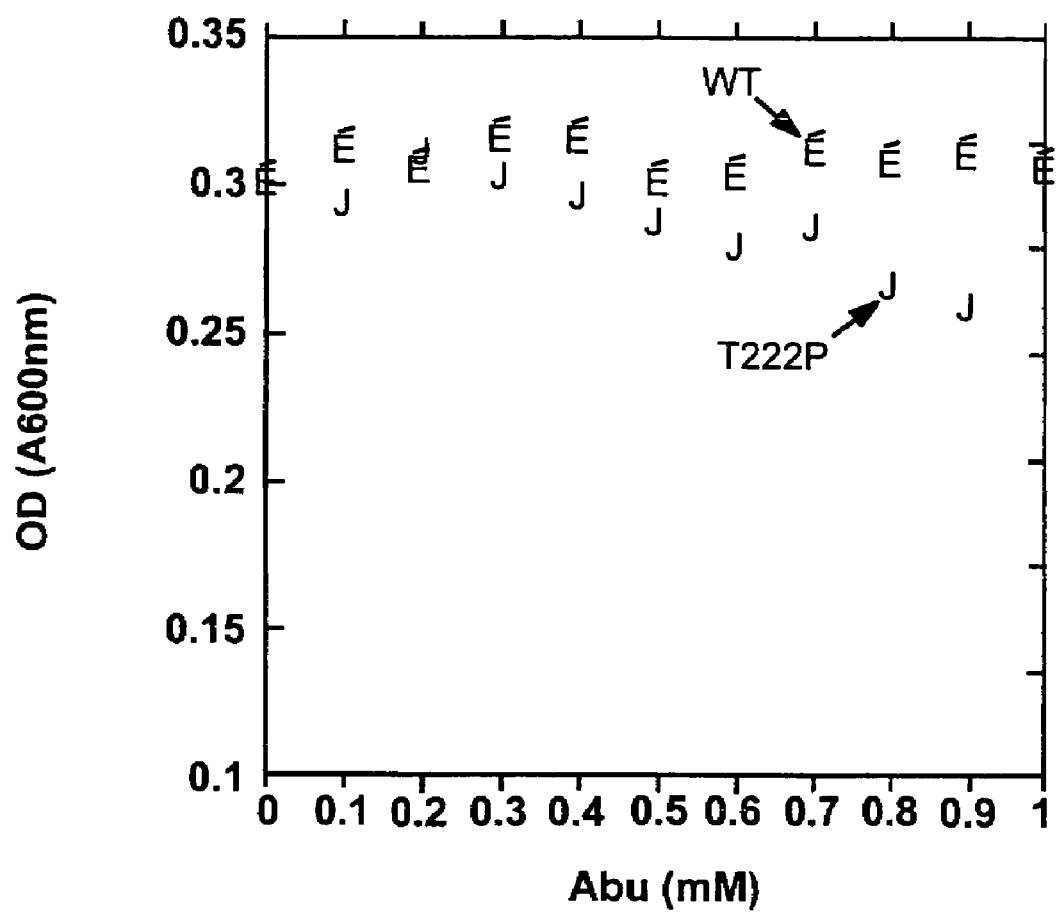

METHOD FOR DIVERSIFYING THE CHEMICAL COMPOSITION OF PROTEINS PRODUCED IN VIVO BY GENETICALLY DISABLING THE EDITING FUNCTION OF THEIR AMINOACYL TRNA SYNTHETASES

CROSS-REFERENCE TO RELATED APPLICATIONS

This application is a continuation of application Ser. No. 10/126,448, filed on Apr. 19, 2002, now abandoned and claims the benefit of priority from provisional application 60/285,495 filed on Apr. 19, 2001.

STATEMENT REGARDING FEDERALLY-SPONSORED RESEARCH

This invention was made with United States Government support under Contract No. GM 23562 awarded by the National Institutes of Health. The United States Government may have certain rights in this invention.

FIELD OF THE INVENTION

The present invention is directed to a method to diversify the chemical composition of proteins produced in vivo, especially to methods comprising the step of disabling, particularly by mutagenesis, the editing function of one of its aminoacyl tRNA synthetases. The present invention is also directed to nucleic acid sequences encoding such mutated aminoacyl tRNA synthetases having their editing site mutated and capable of mischarging its cognate tRNA with a noncanonical amino acid. Also described herein is an improved method for obtaining transformed cells capable of synthesizing in vivo proteins comprising at least a noncanonical amino acid and their use for the production of such proteins.

BACKGROUND OF THE INVENTION

Aminoacyl tRNA synthetases establish the rules of the genetic code by catalyzing the aminoacylation of transfer RNAs. The chemical invariance of the twenty amino acid building blocks of proteins is well established. The only known extensions to this invariant set are formyl-methionine (1) and selenocysteine (2), both incorporated in response to punctuation signals during translation in certain organisms.

Thus, although species have colonized dissimilar terrestrial habitats throughout geological times, this diversification has not been mirrored in the evolution of organisms to include specialized sets of amino acids. For instance, thermophilic, mesophilic, and psychrophilic organisms all assemble proteins by combining the same types of twenty canonical amino acids into different protein sequences. Standing as the "missing link" between alanine and valine (3), aminobutyrate (Abu, also known as butyrine) can be generated by transamination from the physiological metabolite 2-oxo-butyrate and should thus be considered as a latent metabolite (4). Its absence is therefore particularly conspicuous in the proteins of extant organisms.

The selection of amino acids for protein synthesis is done by aminoacyl tRNA synthetases. Typically, each of twenty synthetases catalyzes the attachment of its cognate amino acid to the 3'-end of its cognate tRNA and amino acids are, in this way, associated with specific triplets of the genetic code (5). The active site of several of these enzymes inherently lack the capacity to discriminate between closely similar amino acids at a level sufficient to explain the high accuracy of the code. For that reason, a given enzyme may misactivate closely similar (in size and shape) amino acids at a low frequency (0.1 to 1%) (6). To correct these errors, in many cases, a hydrolytic editing function, at a separate active site, has developed (7-10). One example of a synthetase that has editing activity is valyl-tRNA synthetase (ValRS), which misactivates the isosteric natural amino acid Thr (9), as well as the non-natural Abu (11). Misactivation of these amino acids leads to transient mischarging of tRNA$^{Val}$, followed by hydrolytic deacylation (editing) of the mischarged amino acid from the tRNA.

The present work aimed to establish conditions of artificial selection that promoted usage of non-canonical amino acids, such as Abu, that were not retained by natural selection. Others have attempted to incorporate a non-canonical amino acid into a protein by introducing a foreign, "orthogonal" tRNA/synthetase pair that can insert the amino acid at a specialized stop codon (12).

However, such approaches are laborious, as they require selection, identification, cloning, and study of individual mutant strains.

In order to facilitate the in vivo production of proteins comprising noncanonical amino acids, it would be desirable to have a rapid and generalized method allowing to genetically modify and select cells capable of achieving the in vivo production of such proteins.

Such a desirable method will allow to enlarge the chemistry of translation by having a non-canonical amino acid "infiltrate" all of the codons normally associated with one of the natural amino acids. Indeed, by assigning two amino acids (a cognate and a non-cognate) to a specific set of codons so as to provide a selective advantage to the reprogrammed cells, global changes in the amino acid compositions of all cellular proteins could be made. The present invention addresses this need.

SUMMARY OF THE INVENTION

The present invention provides a general method to diversify the chemical composition of proteins produced in vivo by a cell comprising the step wherein the editing function of an aminoacyl tRNA synthetase of said cell has been disabled.

This rapid and general method may be used to obtain cells comprising a mutation in the DNA sequence encoding the editon domain of said disabled aminoacyl tRNA synthetase compared to the wild type aminoacyl tRNA synthetase coding sequence.

In general, the method of the present invention includes: a) selecting a cell strain wherein the editing function of at least one of the cell's aminoacyl tRNA synthetases has been disabled, said disabled editing function allowing the aminoacyl tRNA synthetase to mischarge the cognate tRNA with said at least one noncanonical amino acid; b) culturing the selected strain in a culture medium comprising said noncanonical amino acid, or one of its precursor, under conditions favourable for the growth of said strain; and c) recovering from the culture medium or from the cells obtained in step b) the proteins containing said noncanonical amino acid.

In various embodiments, the editing function of the aminoacyl tRNA synthetases has been disabled by mutagenizing the DNA sequence encoding the editing domain of an aminoacyl tRNA synthetase in the target cell, said mutagenesis being carried out in the cell preferably by homologous recombination or allele replacement vector leading to an aminoacyl tRNA synthetase variant having an amino acid mutation in its editing domain, said mutation allowing the aminoacyl tRNA synthetase variant to mischarge its cognate tRNA with one noncanonical amino acid.

In a particular related aspect, the present invention is directed to a method for selecting an aminoacyl tRNA synthetase variant capable of mischarging its cognate tRNA with a noncognate amino acid, preferably a noncanonical amino acid, including the steps of: a) elaborating a DNA construct encoding an aminoacyl tRNA synthetase variant having an amino acid mutation in its editing domain; b) transforming a host cell with said DNA construct; c) assaying the ability of the recombinant aminoacyl tRNA synthetase variant produced by said transformed host cell for its ability to mischarge its cognate tRNA with a noncognate amino acid, preferably a noncanonical amino acid; and d) if appropriate, selecting the assayed aminoacyl tRNA synthetase variant if said assayed aminoacyl tRNA synthetase variant is capable of mischarging its cognate tRNA (tRNA(s) associated with the assayed aminoacyl tRNA synthetase) with a noncognate amino acid, preferably with a noncanonical amino acid.

In a further aspect, the invention relates to isolated aminoacyl tRNA synthetase variants capable of mischarging its cognate tRNA with a noncognate amino acid, preferably with a noncanonical amino acid, wherein the nucleic fragment encoding the editing site comprises at least one mutation leading to an amino acid mutation, preferably an amino acid substitution, in the editing site of said aminoacyl tRNA synthetase. Isolated nucleic acid encoding such aminoacyl tRNA synthetase variants, vectors, such as plasmid, and cell comprising such nucleic acid also form part of the present invention.

In another preferred embodiment, the present invention is directed to a method for the production of proteins comprising a noncanonical amino acid including the general steps of: a) culturing, in a culture medium containing said noncanonical amino acid, or one of its precursors, a transformed host cell comprising an aminoacyl tRNA synthetase allele variant capable of mischarging its cognate tRNA with said noncanonical amino acid ; and b) recovering and, if appropriate, purifying the proteins comprising said noncanonical amino acid from the culture medium (supernatant) and/or from the cells (from cells pellet) of step a).

In a final aspect, the invention provides proteins comprising a noncanonical amino acid obtained by the above method.

Other features and advantages of the invention will be apparent from the following description of the preferred embodiments thereof, and from the claims.

BRIEF DESCRIPTION OF THE DRAWINGS

FIGS. 1A to 1C. Suppression and toxicity phenotypes. Amino acid gradient plates were prepared using minimal medium (27).

FIG. 1A: A schematic showing the structures of cysteine, S-carbamoyl-cysteine, valine, threonine and α-aminobutyric acid.

FIG. 1B: Photographs showing the results of experiments demonstrating the cysteine-suppression phenotype. Cysteine (100 μl (0.4 M)) was loaded in a central well after spreading and drying 0.5 ml of a 5/1000 dilution of an overnight culture (in MS glucose medium containing thymidine (0.3 mM)) of β5456 (thyA::erm+ ΔnrdD::kan+ valS:T222P pTS13 (bla+ thyA:146GUA)). Ile-Val (0.3 mM) was added in one plate as a control. The dipeptide Ile-Val was purchased from Bachem A G (Bubendorf, Switzerland). Plates were incubated for 2 days at 30° C.

FIG. 1C: Photographs showing the results of growth of a strain carrying the valS:T222P allele in the presence of L-threonine or Abu. Minimal medium plates supplemented with thymidine (0.3 mM) were pretreated with amino acid solutions by streaking either with Thr (50 μl (0.2 M)) or Abu (50 μl (0.1 M)) vertically along the diameter of the plate to create an amino acid gradient. Mutant (β5456) and wild-type (β5419 (thyA::erm+ ΔnrdD::kan+ pTS13 (bla+ thyA:146GUA)) strains were then streaked horizontally across the plates and incubated for 2 days at 37° C.

FIGS. 2A to 2C. Point mutations in the editing site and their consequences.

FIG. 2A: A schematic showing the positions of the five point mutations isolated in the editing site of ValRS are shown. The IleRS editing site (CP1) (28, 29) that intersects the alternating β-strands (pentagons) and α-helices (rectangles) of the catalytic domain is shown. Alignment of residues in the editing sites of IleRS and ValRS is also shown, with the strictly conserved residues among all published sequences labeled with a colon. Abbreviations are Ec, *Escherichia coli*; Sc, *Saccharomyces cerivisiae*; Hs, *Homo sapiens*.

FIG. 2B: A graph showing misaminoacylation of tRNA$^{Val}$ with Thr by the T222P mutant enzyme at pH 7.5 and 37° C. The wild-type (WT) and mutant alleles were cloned under the control of a $P_{BAD}$ promoter (30). The enzymes were partially purified from a laboratory strain lacking the chromosomal copy of the valS gene (ΔvalS::kan+). The purification and aminoacylation procedures were adapted from Hendrickson et al. (31). (Main panel) Misaminoacylation of tRNA$^{Val}$ with Thr by the two enzymes. (Inset) Aminoacylation of tRNA$^{Val}$ with Val by the two enzymes.

FIG. 2C: A schematic showing MALDI analysis demonstrating In vivo incorporation of aminobutyrate. The His-tagged protein AlaXp was expressed in two Δilv strains containing the wild-type valS or the mutant valS:T222P allele, in MS medium containing Ile-Leu (0.3 mM), Ile-Val (0.02 mM) and Abu (0.2 mM). AlaXp was purified with Ni-NTA agarose (Qiagen GmbH, Hilden, Germany), cut out of a SDS-PAGE preparative gel and prepared for MALDI and μ-LC-MS/MS mass analysis (32). The MALDI-MS analyses were performed in a Voyager-Elite time-of-flight mass spectrometer with delayed extraction (PerSeptive Biosystems, Inc., Framingham, Mass.). The spectrum for peptide Lys156-Arg172 with mass 2097.04 is shown on the bottom panel (wild-type cells). The top panel shows the peptide resolved into two components when isolated from cells bearing the T222P allele of the gene for ValRS. The second component has a mass of 2083.04, exactly 14 mass units less then the "wild-type peptide". Multiple peaks correspond to $^{13}$C isotopic forms that separate peptides differing by 1, 2, 3, etc. mass units.

FIG. 3. A graph showing the results of growth of the valine auxotroph CU505 in the presence of a limiting supply of valine and increasing concentrations of Abu. Overnight cultures of Δilv auxotrophs containing the WT valS (E) or the mutant valS:T222P allele (J) and grown in MS glucose medium with limiting valine (0.04 mM Ile-Val. 0.3 mM Ile-Leu) were diluted 1/1, the Val concentration was adjusted to 0.02 mM and the biomass was determined by measuring the optical density at 600 nm after 24 h of growth at 30° C.

(mutant IleRS having 11 alanine residues in position aa 239-250); (diamond, ♦): IleS wt (wild type IleRS)

Figure 5A:
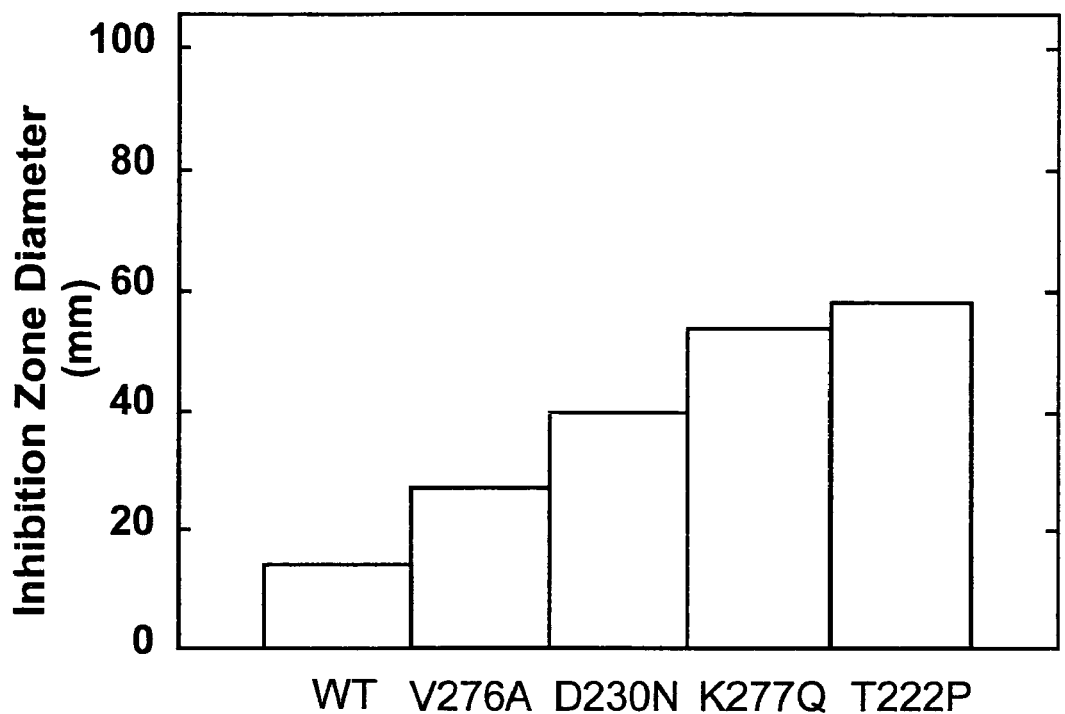
Figure 5B:
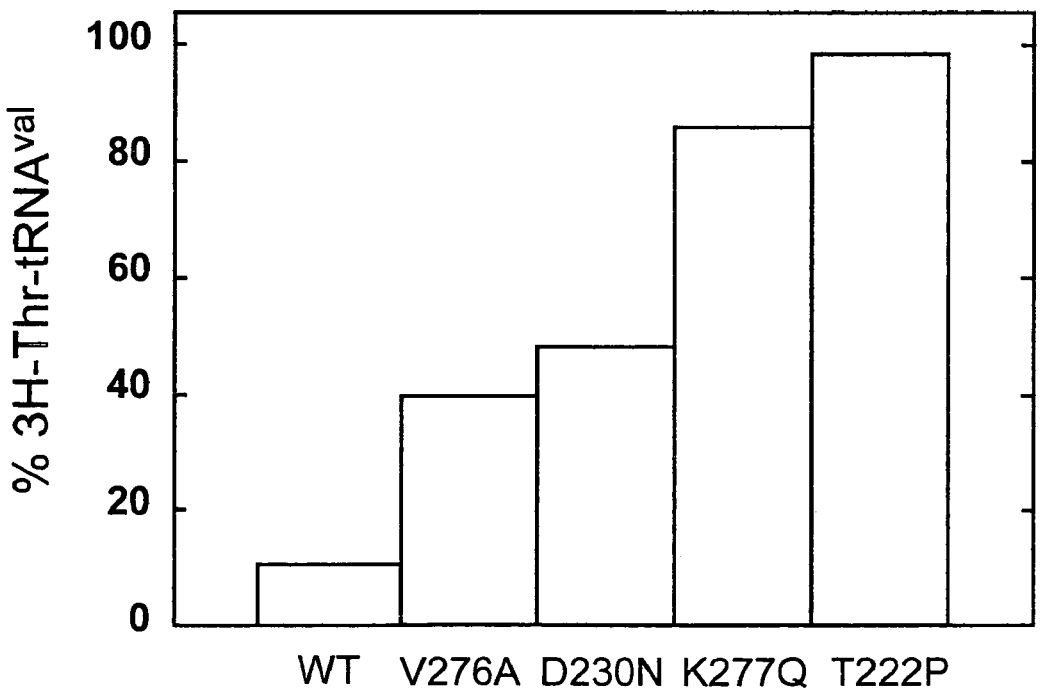

FIGS. 5A and 5B: Correlation of Abu toxicity phenotypes and effectiveness of deacylation by mutant enzymes.

FIG. 5A: Noncognate amino acid toxicity phenotypes. ValS null strains harboring each of the ValRS mutant enzymes in trans were plated on minimal medium. Abu (alpha-aminobutyrate) was loaded into a central well and plates were incubated for 24 hours at 42 deg. C. Degree of toxicity in response to Abu was evaluated by the diameter of the region of inhibited cell growth. Strains bearing the K277Q and T222P mutant valS alleles showed the most severe response to Abu. The growth of D230N valS was inhibited by high concentrations of Abu but the effect was not observed at lower concentrations. The V276A mutation introduces a slight sensitivity to Abu. Similar phenotypes were observed in response to exogenous threonine (data not shown).

FIG. 5B: Histogram representation of the inhibition zone diameters of DvalS::kanR strains harboring each of the ValRS editing mutants on plasmid in response to exogenous Abu. Effects range from mild to severe. Histogram representation of the percentage of mischarged Thr-tRNAVal remaining after incubation with 2 nM enzyme for 15 minutes at room temperature. Both show a distinct range in the severity of editing defects caused by these point mutations. Taken together this illustrates a correlation between the ability of the mutant enzyme to deacylate mischarged amino acids from tRNAVal in vitro and the degree of in vivo toxicity.

DETAILED DESCRIPTION OF THE INVENTION

The present invention provides a method to diversify the chemical composition of proteins produced in vivo by a cell comprising the step of disabling the editing function of one of its aminoacyl tRNA synthetases.

The phrase "a step of disabling the editing function of an aminoacyl tRNA synthetase", is intended to designate a step through which a mutant strain is obtained wherein an allele coding for an aminoacyl tRNA synthetase comprises a mutation in its editing site or domain resulting in:

the loss of the role of the editing function in restricting the genetic code to 20 amino acids;

the loss of the role of the editing function in preventing the invasion of noncognate amino acid; and/or the misactivation of noncognate amino acids or/and the non hydrolyzation of generated "noncognate amino acid-tRNA" normally hydrolyzed by the editing function of the wild type cognate aminoacyl tRNA synthetase, these alterations of the editing function inducing the potential misincorporation of a noncognate amino acid, preferably a noncanonical amino acid, in place of the cognate amino acid charged by the aminoacyl tRNA synthetase encoded by the wild type allele.

For example, such a step of disabling the editing function of one of an aminoacyl tRNA synthetase may comprise a step of:

selecting a mutant strain comprising an aminoacyl tRNA synthetase natural variant having a mutation in its editing domain resulting to these above cited editing function alterations; or preferably selecting a mutant strain comprising an aminoacyl tRNA synthetase variant having a mutation in its editing domain resulting to these above cited editing function alterations, this variant being obtained by mutagenesis, such as by homologous recombination or replacement allele vector or by any mutagenesis methods known by the skilled person capable of introducing such a mutation, preferably integrated into the genome of the cell.

The term "cognate amino acid" as used in the present specification is intended to designate the amino acid normally charged by the tRNA corresponding to (or associated with) the aminoacyl tRNA synthetase wild type (for example: the cognate amino acid for valyl-tRNA synthetase is valine).

By the term "cognate tRNA" as used in the present specification is intended to designate the tRNA corresponding to (or associated with) the aminoacyl tRNA synthetase wild type (for example: the cognate tRNA for valyl-tRNA synthetase is $tRNA^{Val}$).

In an additional embodiment of the present invention, is provided a method for producing in vivo proteins comprising at least one noncanonical amino acid comprising the step of:

a) selecting a cell strain wherein the editing function of one of its aminoacyl tRNA synthetases has been disabled by mutagenesis, said disabled editing function allowing the aminoacyl tRNA synthetase to mischarge the cognate tRNA with said at least one noncanonical amino acid;

b) culturing the selected strain in a culture medium comprising said noncanonical amino acid, or one of its precursor, under favourable conditions for the growth of said strain; and c) recovering from the culture medium or from the cells obtained in step b) the proteins containing said noncanonical amino acid.

By "favourable growth conditions" is meant an environment that is relatively favorable for cell growth and/or viability. Such conditions take into account the relative availability of nutrients and optimal temperature, atmospheric pressure, presence or absence of gases (such as oxygen and carbon dioxide), and exposure to light, as required by the organism being studied.

By "precursor" is meant a compound which can be efficiently converted in vivo by the cell in said noncanonical amino acid.

In a preferred embodiment, the cell strain wherein the editing function of one of its aminoacyl tRNA synthetases has been disabled, comprises a mutation in the DNA sequence encoding the editing domain of said disabled aminoacyl tRNA synthetase compared to the wild type aminoacyl tRNA synthetase coding sequence.

In a more preferred embodiment, said DNA mutation leads to an amino acid mutation, preferably an amino acid substitution, more preferably an amino acid single substitution, in the editing domain of said aminoacyl tRNA synthetase.

In another preferred embodiment is provided a method according to the present invention, wherein the disabled aminoacyl tRNA synthetase is capable of mischarging its cognate tRNA with a canonical amino acid sterically similar to the amino acid charged by the wild type aminoacyl tRNA synthetase on its cognate tRNA.

In another preferred embodiment is provided a method according to the present invention, wherein the disabled aminoacyl tRNA synthetase is capable of mischarging its cognate tRNA with a noncanonical amino acid sterically similar to the amino acid charged by the wild type aminoacyl tRNA synthetase on its cognate tRNA.

In another aspect of the present invention, there is provides a method for obtaining cells capable of producing in vivo proteins comprising at least one noncanonical amino acid comprising the step of mutagenizing the DNA sequence encoding the editing domain of an aminoacyl tRNA synthetase in a cell, said mutagenizing leading to an aminoacyl tRNA synthetase variant having an amino acid mutation in its editing domain and said mutation allowing the aminoacyl tRNA synthetase variant to mischarge its cognate tRNA with said at least one noncanonical amino acid.

In preferred embodiment, there is provides a method for obtaining cells capable of producing in vivo proteins comprising at least one noncanonical amino acid according to the present invention, comprising the steps of:
a) assaying the ability of an aminoacyl tRNA synthetase variant mutated in its editing domain for its ability to mischarge its cognate tRNA with a noncanonical amino acid;
b) mutagenizing the DNA sequence encoding the editing domain of said aminoacyl tRNA synthetase in a cell, said mutagenizing leading to replace the allele encoding the wild type aminoacyl tRNA synthetase by an allele encoding the aminoacyl tRNA synthetase variant assayed in step a) and capable of producing detectable noncanonical amino acid mischarging;
c) optionally, identifying, selecting and/or cloning the cells containing such aminoacyl tRNA synthetase variant having the ability to mischarge one noncanonical amino acid.

In a preferred embodiment, the cell wherein the editing domain of the aminoacyl tRNA synthetase has been disabled, preferably by mutagenesis, is a microbial or animal cell, preferably a bacterium, a yeast or a fungus, more preferably a bacterium such as *Escherichia coli* or *Acinetobacter*.

In another preferred embodiment of the present invention, is provided a method, wherein the editing domain of the aminoacyl tRNA synthetase of the target cell has been disabled by by homologous recombination or by recombination into the genome of the target cell using an allelic replacement vector.

The oligonucleotides comprising the nucleic fragment encoding the mutated editing site, or portion thereof, and which contain the mutation to be introduced into the wild type allele of the target cell, can be chemically synthetized or synthetized by Polymerase Chain Reaction (PCR).

By microbial or animal cells are preferred cells that undergo homologous recombination. Such cells may be of bacterial, mycobacterial, yeast, fungal, algal, plant, or animal origin.

By "homologous recombination" is meant a process by which an exogenously introduced DNA molecule integrates into a target DNA molecule in a region where there is identical or near-identical nucleotide sequence between the two molecules. Homologous recombination is mediated by complementary base-pairing, and may result in either insertion of the exogenous DNA into the target DNA (a single cross-over event), or replacement of the target DNA by the exogenous DNA (a double cross-over event).

By "allelic replacement vector" is meant any DNA element that can be used to introduce mutations into the genome of a target cell by specific replacement of a native gene with a mutated copy. For example, gene replacement in bacteria is commonly performed using plasmids that contain a target gene containing a mutation and a negative selectable marker outside of the region of homology. Such a plasmid integrates into the target chromosome by homologous recombination (single cross-over). Appropriate selection yields cells that have lost the negative selection marker by a second homologous recombination event (double cross-over) and contain only a mutant copy of the target gene.

In another embodiment, the cell wherein the editing domain of the aminoacyl tRNA synthetase has been disabled or mutagenized may contain a selectable marker gene for identifying and selecting the cells containing the mutagenized DNA. The identification and selection of that cells wherein the editing domain of the aminoacyl tRNA synthetase has been disabled or mutagenized may be based upon the ability of the cells to grow on selective medium, wherein a cell containing the selectable marker can grow on selective medium, and a cell lacking this selectable marker cannot grow, or grows more slowly, on selective medium.

In still another embodiment, the cell wherein the editing domain of the aminoacyl tRNA synthetase has been disabled or mutagenized may contain a reporter gene, for identifying and selecting the cells containing the mutagenized DNA. The identification and selection of that cells wherein the editing domain of the aminoacyl tRNA synthetase has been disabled or mutagenized may be based on a reporter gene assay, wherein the expression by the cell of the reporter gene confirms the disabling or the mutagenesis and a cell lacking the disabling or the mutagenesis does not express the reporter gene.

By "selectable marker" is meant a gene that alters the ability of a cell harboring this gene to grow or survive in a given growth environment relative to a similar cell lacking the selectable marker. Such a marker may be a positive or negative selectable marker. For example, a positive selectable marker (e.g., an antibiotic resistance or auxotrophic growth gene) encodes a product that confers growth or survival abilities in selective medium (e.g., containing an antibiotic or lacking an essential nutrient). A negative selectable marker, in contrast, prevents cells harbouring this gene from growing in negative selection medium, when compared to cells not harbouring this gene. A selectable marker may confer both positive and negative selectability, depending upon the medium used to grow the cell. The use of selectable markers in prokaryotic and eukaryotic cells is well known by those of skill in the art.

By "reporter gene" is meant any gene which encodes a product whose expression is detectable and/or quantitatable by immunological, chemical, biochemical, biological, or mechanical assays. A reporter gene product may, for example, have one of the following attributes, without restriction: fluorescence (e.g., green fluorescent protein), enzymatic activity (e.g., lacZ/.beta.-galactosidase, luciferase, chloramphenicol acetyltransferase, alkaline phosphatase), toxicity (e.g., ricin), or an ability to be specifically bound by a second molecule (e.g., biotin or a detectably labelled antibody). It is understood that any engineered variants of reporter genes, which are readily available to one skilled in the art, are also included, without restriction, in the foregoing definition.

By "identifying cells containing mutagenized DNA" is meant exposing the population of cells transformed with the mutagenized DNA to selective pressure (such as growth in the presence of an antibiotic or the absence of a nutrient) consistent with a selectable marker carried by the cell containing the recombined mutagenized DNA (e.g., an antibiotic resistance gene or auxotrophic growth gene known to those skilled in the art). Identifying cells containing the recombined mutagenized DNA may also be done by subjecting transformed cells to a reporter gene assay. Selections and screens may be employed to identify cells containing the recombined mutagenized DNA, although selections are preferred.

In another aspect, the present invention is directed to a method for selecting an aminoacyl tRNA synthetase variant capable of mischarging its cognate tRNA with a noncognate and/or a noncanonical amino acid, comprising the steps of:
a) elaborating a DNA construct comprising a DNA sequence encoding an aminoacyl tRNA synthetase variant wherein said aminoacyl tRNA synthetase variant has at least an amino acid mutation, preferably a substitution, more preferably a single substitution, in its editing domain compared with the wild type aminoacyl tRNA synthetase;

b) transforming a host cell with the DNA construct of step a) and, after a step of culturing said transformed host cell, recovering and, optionally, purifying the recombinant aminoacyl tRNA synthetase variant expressed by the host cell;

c) assaying the ability of the recombinant aminoacyl tRNA synthetase variant recovered in step b) for its ability to mischarge its cognate tRNA with a noncognate and/or a noncanonical amino acid; and d) selecting said aminoacyl tRNA synthetase variant if detectable mischarging has been produced in step c).

Figure 2B:
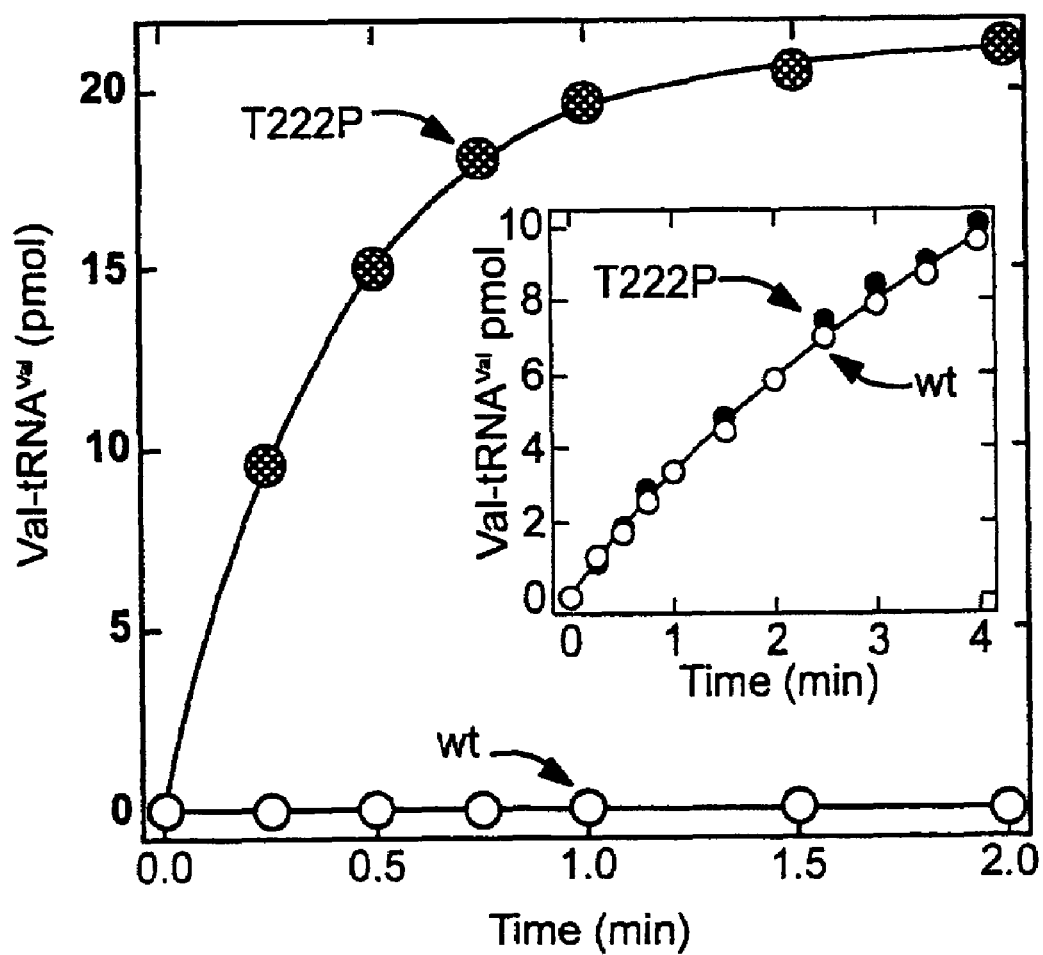

Such methods for assaying the ability of the recombinant aminoacyl tRNA synthetase variant recovered in step b) for its ability to mischarge its cognate tRNA with a noncognate and/or a noncanonical amino acid, are disclosed for example in the following examples (see FIG. 2B). The methods known to those skilled in the art for assaying such an ability may be used.

By "transformation" is meant any method for introducing foreign molecules, such as DNA, into a cell. Lipofection, DEAE-dextran-mediated transfection, microinjection, protoplast fusion, calcium phosphate precipitation, retroviral delivery, electroporation, natural transformation, and biolistic transformation are just a few of the methods known to those skilled in the art which may be used.

In another aspect, the invention provides an isolated aminoacyl tRNA synthetase variant capable of mischarging its cognate tRNA with a noncanonical amino acid, obtainable by the method for selecting an aminoacyl tRNA synthetase variant according to the present invention.

The isolated nucleic acid sequence encoding the aminoacyl tRNA synthetase variant according to the invention or vectors comprising a nucleic acid encoding said aminoacyl tRNA synthetase variant form also part of the present invention.

In another aspect, the invention provides a transformed cell comprising a nucleic acid encoding an aminoacyl tRNA synthetase variant according to the present invention.

In a preferred embodiment, said transformed cells are characterized in that said nucleic acid encoding an aminoacyl tRNA synthetase variant according to the present invention is integrated in the genome of said cell.

In a more preferred embodiment, said transformed cells are characterized in that the nucleic fragment comprising the mutation, preferably a substitution, more preferably a single substitution, leading to the alteration of the editing function of the aminoacyl tRNA synthetase variant, has been integrated into the genome of said transformed cell by using mutagenesis, such as homologous recombination, replacement allele vector or any mutagenesis methods for introducing nucleic acid molecules such as DNA, into a cell, known to those skilled in the art, such as lipofection, DEAE-dextran-mediated transfection, microinjection, protoplast fusion, calcium phosphate precipitation, retroviral delivery, electroporation, natural transformation and biolistic transformation.

The invention also relates to isolated prokaryotic or eukaryotic cells capable of producing a protein the amino acid sequence of which comprises at least one noncanonical amino acid, characterized in that they comprise an aminoacyl-tRNA synthetase variant which is capable of charging onto one of its cognate tRNAs a noncanonical amino acid or an amino acid other than the cognate amino acid, and in that the nucleic acid sequence of the allele encoding said aminoacyl-tRNA synthetase variant includes at least one mutation, preferably a substitution, more preferably a single substitution, compared with the sequence of the corresponding wild-type allele, said at least one mutation integrated into the genome being located on the editing site of said aminoacyl-tRNA synthetase and having been introduced by a technique of mutagenesis, such as genetic recombination.

In another aspect, the invention also comprises the use of a transformed cell according to the invention for producing protein, in particular recombinant protein, the amino acid sequence of which comprises at least one unconventional amino acid.

In a preferred embodiment, the present invention is directed to a method for the production of proteins comprising a noncanonical amino acid characterized in that said method comprises the following steps:

a) culturing a transformed cell comprising an allele encoding an aminoacyl tRNA synthetase variant according to the invention in a culture medium containing a noncanonical amino acid capable of being mischarged by the cognate tRNA of the aminoacyl tRNA synthetase variant contained in said cell, in a culture medium and under culture conditions which allow the growth of said cell; and b) recovering and, optionally, purifying the proteins comprising said noncanonical amino acid from the culture medium (supernatant) or from the cells (cells pellet) of step a).

Proteins comprising a noncanonical amino acid obtained by the above method according to the invention form also part of the present invention.

The processes for purifying protein, which may be natural or recombinant, conventionally used by those skilled in the art generally employ methods used individually or in combination, such as fractionation, chromatography methods, immunoaffinity techniques using specific mono- or polyclonal antibodies, etc.

The presence of a noncanonical amino acid on the protein to be purified, which noncanonical amino acid could have a specific functional group, may facilitate its purification by reacting selectively with the purification support without modifying the activity of the protein.

Among the proteins which can be produced by a process according to the invention, mention may be made, but without being limited thereto, of proteins which, through the incorporation of at least one noncanonical amino acid, make it possible to obtain a desired activity which a protein the sequence of which includes only canonical amino acids does not make it possible to obtain. The term "activity" is intended to refer, in general, to any activity such as a physiological or biological activity, even partial, relating to unicellular or multicellular organisms, such as for example a structural or biochemical activity, for example an enzymatic or antigenic activity, an activity of antibody type, or an activity which modulates, regulates or inhibits biological activity, or such that it allows the implementation thereof in a process for biosynthesizing or for biodegrading chemical or biochemical compounds.

Among the proteins which can be produced by a process according to the invention, mention may also be made of proteins for which the incorporation of at least one noncanonical amino acid is carried out such that there results therefrom no substantial modification of the biological activity of the corresponding unmodified protein. Besides the conserved biological activity of the corresponding unmodified protein, these proteins according to the invention will have a noncanonical amino acid with specific properties which may be advantageously exploited.

Among the specific properties conferred by the presence of a noncanonical amino acid, mention may be made in particular of the properties linked to the presence of a functional group on said noncanonical amino acid, capable of reacting easily and specifically with a chemical or biochemical compound under conditions which make it possible not to modify the activity of the protein or which avoid modifying the conventional amino acids.

The presence of this specific functional group may advantageously be used, for example, for:

(i) purifying any protein, in particular any recombinant protein, which incorporates said unconventional amino acid;
(ii) coupling such a protein to a solid support;
(iii) coupling to such a protein molecules capable of being detected, such as spectroscopic probes of varied nature;
(iv) coupling to such a protein lipophilic or hydrophilic polymers which allow the solubilization thereof in solvents or which allow masking against recognition by antibodies;
(v) coupling such a protein to a polynucleotide;
(vi) coupling such a protein to a chemical or biochemical compound the presence of which makes it possible to increase, to decrease, to modify, to regulate or to target the biological activity of said protein, or to modify the bioavailability thereof as a compound for therapeutic use; or
(vii) permanently attaching to such a protein a coenzyme which otherwise would diffuse in solution.

Also included in the present invention are the processes according to the invention, characterized in that said transformed cell according to the present invention comprises a homologous or heterologous gene of interest the coding sequence of which includes at least one codon encoding an amino acid the cognate tRNA of which can be mischarged by the aminoacyl tRNA synthetase variant contained in said transformed cell.

In general, the homologous or heterologous gene of interest, which can be isolated by any conventional technique, such as cloning or PCR (Polymerase Chain Reaction), or chemically synthesized, may be chosen from genes encoding any protein which can be used as a therapeutic or cosmetic compound, or as a diagnostic reagent or as a compound which can be used in a biosynthesis or biodegradation process. The protein of interest can consist of a mature protein, a precursor, and in particular a precursor intended to be secreted and comprising a signal peptide, a truncated protein, a chimeric protein originating from the fusion of sequences of diverse origins, or a mutated protein having improved and/or modified biological properties.

The invention also comprises a process for producing a protein according to the invention, characterized in that the culture medium of step a) also comprises the compounds required for inducing the synthesis of the protein encoded by said homologous or heterologous gene of interest. These compounds are known to those skilled in the art and depend, in particular, on the cell and on the homologous or heterologous gene selected.

In any of the method according to the present invention, it is preferred that said aminoacyl tRNA synthetase is an aminoacyl tRNA synthetase selected from the group consisting of the aminoacyl tRNA synthetase comprising an editing function corresponding to an editing site or domain encoded by a portion of the DNA encoded said aminoacyl tRNA synthetase, preferably encoded by a DNA portion having at least conserved residues compared after alignment with the editing site of the valyl-tRNA synthetase and isoleucyl-tRNA synthetase as shown in FIG. 2A, preferably selected from the group consisting of the aminoacyl tRNA synthetase valyl-tRNA synthetase, isoleucyl-tRNA synthetase, leucyl-tRNA synthetase, alanyl-tRNA synthetase, prolyl-tRNA synthetase, threonyl-tRNA synthetase, phenyl-tRNA synthetase and lysyl-tRNA synthetase which are known to have an editing site or domain (see for Ile RS Baldwin, A. N. and Berg, P. (1966) J. Biol. Chem. 241, 839-845 and Eldred, E. W. and Schimmel, P. R. (1972) J. Biol. Chem. 247, 2961-2964; for Val RS, Fersht, A. R. and Kaethner, M. M. (1976) Biochemistry. 15 (15), 3342-3346; for Leu RS, English, S. et al., (1986) Nucleic Acids Research. 14 (19), 7529-7539; for Ala RS, Tsui, W. C. and Fersht, A. R. (1981) Nucleic Acids Research. 9, 7529-7539; for Pro RS, Beuning, P. J. and Musier-Forsyth, K. (2000) PNAS. 97 (16), 8916-8920; for Thr RS, Sankaranarayanan, R. et al., (2000) Nat. Struct. Biol. 7, 461-465 and Musier-Foryth, K. and Beuning, P. J. (2000) Nat. Struct. Biol. 7, 435-436; for PheRS, Yarus, M. (1972) PNAS. 69, 1915-1919 and for LysRS, Jakubowski, H. (1997) Biochemistry. 36, 11077-11085.

EXAMPLES

Example 1

A direct selection for restoring an enzymatic activity through incorporation of Abu could not be easily set up because its aliphatic side chain lacks chemical reactivity and therefore cannot act as a catalytic residue. We thus resorted to an indirect scheme based on the structural resemblance of Abu with Cys (FIG. 1A), an essential catalytic residue in numerous enzymes. Selecting a synthetase mutant that mischarged its cognate tRNA with Cys might result in Abu being mischarged by the mutant synthetase.

We took advantage of the thyA conditional selection screen in *E. coli*, based on the absolute requirement for an active thymidylate synthase when thymidine is not provided as a growth factor (13). This same screen was used previously to assess the potency of suppressor Cys-tRNAs in codon misreading (14) and to enforce phenotypic suppression by the non-canonical azaleucine (15). An entire set of plasmid-borne thyA alleles with all 64 different codons at position 146 was constructed for altering the catalytic site occupied by an essential Cys (16, 17). Each allele was tested for its ability to restore growth to an *E. coli* strain (lacking the chromosomal copy of thyA) on mineral glucose medium in the absence of thymidine (14, 15). Three of the 64 plasmid-borne thyA alleles restored growth. These had one of three codons-UGU, UGC, or UGA. The growth responses of the UGU and UGC alleles were expected, as these code for cysteine. The positive response of UGA (a termination codon in *E. coli*) likely results from read-through by Cys-tRNA, and thus demonstrates the sensitivity of the selection assay.

Strains bearing inactive alleles of thyA were then tested to see if they could be suppressed by supplying them with excess L-cysteine in mineral medium devoid of thymidine. Shallow growth was reproducibly observed on L-cysteine gradient plates (18) for the missense alleles having any of the eight codons AUN and GUN alone. Growth was stronger with alleles bearing any of the four Val codons (GUU, GUC, GUA, and GUG) than for those with the three Ile codons (AUU, AUC, and AUA) or for the Met codon AUG. Cysteine-suppression of the three Ile codon-bearing alleles and of the Met codon-bearing allele was abolished by addition of exogenous L-isoleucine and L-methionine, respectively. Suppression of the four Val codon-bearing alleles was abolished by addition of exogenous L-valine plus L-isoleucine but not by L-isoleucine alone (18). The four Val146 alleles gave a similar growth response in cysteine gradient plates, despite being decoded by three different tRNA$^{Val}$ isoacceptors, thus suggesting that Cys is being mischarged onto all three Val isoacceptor tRNAs by ValRS. Altogether, these results suggested that ValRS catalyzed the formation of Cys-tRNA$^{Val}$ in vivo at a rate sufficient for active thymidylate synthase production and that this mischarging reaction was prevented by increasing the intracellular concentration of L-valine. This interpretation is in line with earlier reports of Cys misactivation by ValRS in vitro (11).

Suppression of thyA:Val146 alleles was weak on plates and required high L-cysteine concentrations (developed from a gradient starting at a concentration of 100 mM). It could thus be anticipated that a scarce L-cysteine supply should select for an enhanced efficiency of phenotypic suppression. Two experimental procedures were followed to this end. In the first procedure strain β5519 (thyA::erm+ ΔnrdD::kan+ pTS13 (bla+ thyA:146GUA) was propagated over 100 generations in serial liquid culture with limiting cysteine (1.5 mM) under anaerobic conditions resulting in isolation of strain β5420 (19). The second procedure relied on a one-step selection under aerobic conditions on plates containing a non-oxidizable precursor that is inefficiently converted into cysteine by E.coli (S-carbamoyl-cysteine (Scc, FIG. 1A) (19)). A mutator marker (dnaQ or mutS) was introduced into the test strain β5519 to increase the frequency above 10$^{-10}$ of Scc-suppressible thymidine auxotrophs (19). This approach resulted in the isolation of four strains: β5456, β5479, β5485 and β5486. All five isolated strains were found not to grow at 42, in agreement with the heat sensitivity generally caused by translational errors (20). The cysteine-suppression phenotype is shown for one of these strains (β5456) in FIG. 1B, together with its abolition by L-valine (supplied as an Ile-Val peptide).

Judging from these phenotypes, mutations in the valS gene for valyl-tRNA synthetase were suspected for each isolated strain. To test for this possibility, we took advantage of the nrdD::kan+ marker (19) located 0.4 min from valS on the E. coli chromosome. For the five mutants, the trait of cysteine- or Scc-suppressible thymidine auxotrophy was indeed found to co-transduce with the nrdD::kan+ marker in a proportion of about 45%. Further characterization of the valS mutations was performed by PCR-amplification followed by sequencing of five nrdD::kan+ transductants exhibiting Scc-suppressible thymidine auxotrophy derived from the five isolated strains (21). As shown in Table 1, each of the five mutants contained a single amino acid substitution at positions within the conserved editing domain (known as CP1) of ValRS (22). The following mutations were identified: T222P, R223H, D230N, V276A, and K277Q. Remarkably, two of these positions (T222 and D230) align with conserved positions in IleRS that had been demonstrated previously to be involved in the hydrolytic editing of misacylated Val-tRNA$^{Ile}$ (23) (FIG. 2A).

TABLE 1

Mutations of the valS gene selected by suppression of the thymidine auxotrophy of strain β5419 (ΔthyA::erm+ ΔnrdD::kan+pTS13 (bla+ thyA:146GUA)).

| Strain | Method of isolation | Mutator genotype | \multicolumn{5}{c}{Codon of valS} | | | | |
|---|---|---|---|---|---|---|---|
| | | | 222 | 223 | 230 | 276 | 277 |
| β5419 | — | wt | ACC<br>Thr | CGT<br>Arg | GAT<br>Asp | GTG<br>Val | AAA<br>Lys |

TABLE 1-continued

Mutations of the valS gene selected by suppression of the thymidine auxotrophy of strain β5419 (ΔthyA::erm+ ΔnrdD::kan+pTS13 (bla+ thyA:146GUA)).

| Strain | Method of isolation | Mutator genotype | 222 | 223 | 230 | 276 | 277 |
|---|---|---|---|---|---|---|---|
| β5456 | Selection on Scc | ΔdnaQ | CCC<br>Pro | CGT | GAT | GTG | AAA |
| β5479 | Selection on Scc | ΔmutS | ACC | CAT<br>His | GAT | GTG | AAA |
| β5486 | Selection on Scc | ΔmutS | ACC | CGT | AAT<br>Asn | GTG | AAA |
| β5485 | Selection on Scc | ΔmutS | ACC | CGT | GAT | GCG<br>Ala | AAA |
| β5520 | Selection on Cys under anaerobiosis | wt | ACC | CGT | GAT | GTG | CAA<br>Gln |

ValRS is known to misactivate Thr and generate Thr-tRNA$^{Val}$, which normally is hydrolyzed by the ValRS editing activity (9). If the ValRS mutants in Table 1 are impared for editing, then strains bearing each of these mutations should misincoporate Thr into protein, and L-threonine would then be toxic in these strains. The growth of the five different valS strains was therefore tested in the presence of L-threonine. All displayed high sensitivity towards exogenous L-threonine (at 2 mM), while the parent strain β5419 was insensitive to L-threonine at all concentrations. The results for the strain carrying the valS:T222P allele are shown in FIG. 1C.

The phenotype of the valS:T222P allele suggested that the T222P enzyme mischarged tRNA$^{Val}$ with Thr and Cys in vivo. The T222P mutant enzyme was, therefore, expressed and partially purified so that it could be directly assayed for the ability to misacylate tRNA$^{Val}$. The purified enzyme had the same activity as the wild-type enzyme for charging with valine (FIG. 2B, inset). In contrast, the T222P mutant enzyme misacylated tRNA$^{Val}$ with Thr to give Thr-tRNAV$^{Val}$ while the wild-type enzyme produced no detectable mischarged tRNA$^{Val}$ (FIG. 2B). Misacylation of tRNA$^{Val}$ with cysteine was also catalyzed only by the mutant enzyme.

Figure 2C:
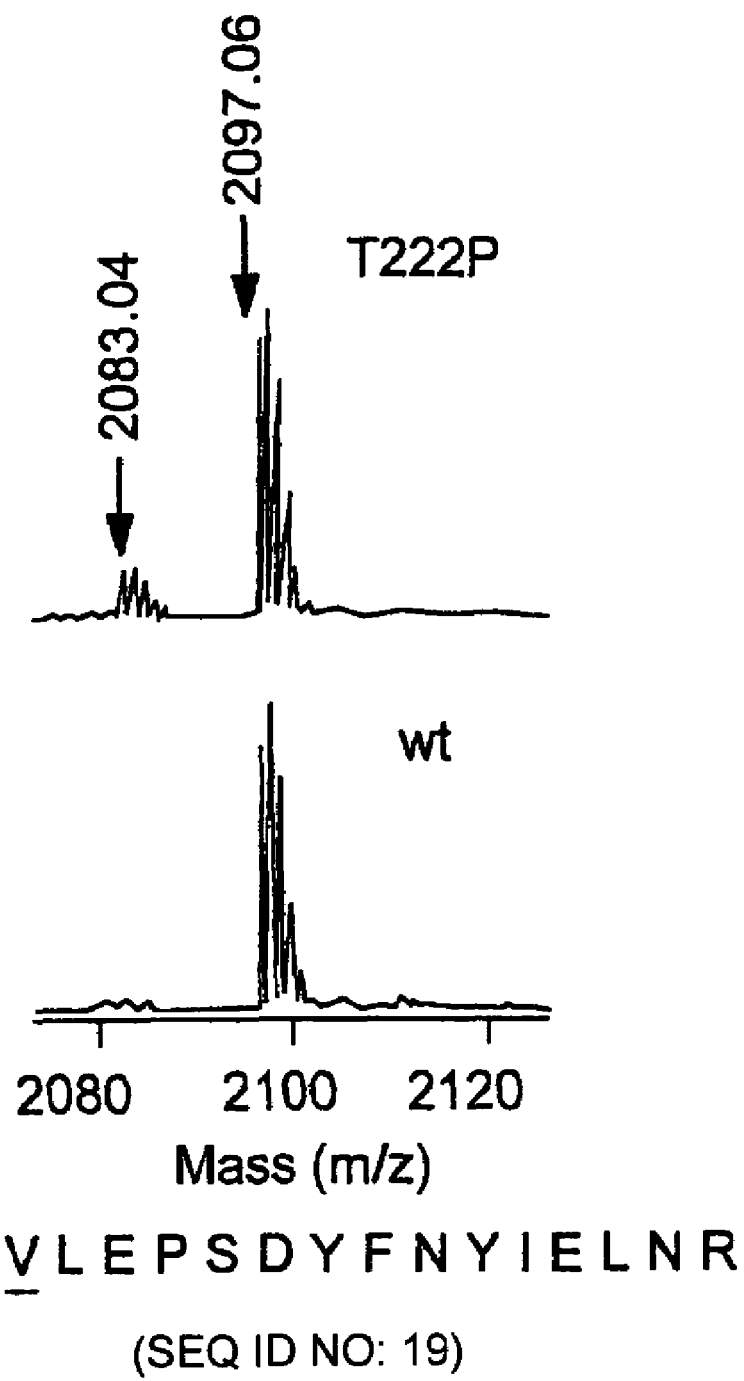

We anticipated that ValRS mutants that misincorporated Cys would also misincorporate Abu. Indeed, the strain carrying the valS:T222P allele on the chromosome (β5456) was sensitive to Abu (FIG. 1C) (whereas its wild-type counterpart was not), suggesting incorporation of Abu in response to Val codons. With this in mind, we showed that Abu could contribute to the relief of L-valine auxotrophy of the Δilv strain CU505, but only in the presence of the valS:T222P allele (19). Whole cell protein was isolated from strain CU505 grown in the presence of Abu (0.2 mM), in the presence or absence of the valS:T222P allele in the host cell. Analysis of amino acid composition showed that 24% of the valine was replaced by Abu only in the strain harboring the mutant allele (Table 2). Finally, the valine-rich yeast protein AlaXp (swisprot:P53960) was overexpressed and purified from strains containing the valS:T222P allele grown in the presence of Abu. The protein samples were digested by trypsin and analyzed by mass spectrometry. MALDI analysis showed that, when AlaXp was produced in the strain carrying the T222P mutation, it contained a mixture of Val and misincorporated Abu (FIG. 2C). For a given peptide the degree of misincorporation ranged between 9.5% and 18% per Val codon. Sequencing of several Abu-containing peptides confirmed that Abu was specifically misincorporated into positions designated by Val codons.

Table 2. Incorporation of Abu into cells bearing wild-type and T222P mutant alleles of valS. Cultures of the Δilv strain CU505 (19) and the isogenic strain β5498 carrying the valS: T222P allele were grown overnight in minimal medium (27) with Ile-Leu (0.3 mM) and limiting valine (0.04 mM Ile-Val), diluted (1/2), and adjusted with Ile-Val (0.02 mM) with or without Abu (0.2 mM). After 24 hours of growth, total protein was extracted as follows. Cells were first harvested by centrifugation and washed in cold 10% trichloroacetic acid (TCA, 1/2 of the culture volume). Cells were then re-centrifuged at 4000×g for 10 min, resuspended in cold 10% TCA (1/10 of the culture volume) and centrifuged again. The washed cells were resuspended in % TCA, heated at 95° C. for 30 minutes and centrifuged (4000×g, 10 min). The precipitate was washed three times with cold acetone and dissolved in 50 mM $NH_4HCO_3$. Proteins were hydrolyzed in 6 N HCl-0.2% phenol at 110C. for 20 h in sealed tubes. Norleucine was added as an internal standard. Aliquots of the hydrolysates were analyzed on a Beckman 6300 Amino Acid Analyzer. Amino acids were quantified by appropriate standards and values are presented relative the wild-type (WT) control that lacked Abu.

| Amino acid incorporated | WT | T222P | WT + Abu | T222P + Abu |
|---|---|---|---|---|
| Abu | 0.0 | 0.0 | 0.0 | 0.24 |
| Val | 1.0 | 0.95 | 1.0 | 0.73 |
| Val + Abu | 1.0 | 0.95 | 1.0 | 0.97 |
| Ile | 1.0 | 1.0 | 1.0 | 1.0 |
| Ala | 1.0 | 0.97 | 1.0 | 0.92 |

Example 2

Directed evolution scheme. To avoid a decrease of cysteine concentration in the medium due to oxidation, the selections were carried out under strictly anaerobic conditions. The biomass of cells in cultures relative to the cysteine concentration (measured as optical density at 600 nm after 24 h of growth at 30° C.) gradually increased four-fold when the thyA strain β5366 (AthyA::erm+ pTS 13 (bla+ thyA: 146GUA)) was propagated by serial transfer in mineral glucose medium supplemented with 1.5 mM cysteine. A high concentration of cysteine was required because the input population could hardly be propagated otherwise. After 16 inoculations, each at a dilution of 1/100 (a total of about 100 generations), single colonies were isolated on mineral glucose plates supplemented with thymidine (a representative of which was designated strain β5520).

One-step selection scheme. For the one-step selections, cysteine oxidation under aerobiosis and subsequent cystine precipitation from the growth medium was avoided by use of the non-oxidizable precursor S-carbamoyl-cysteine (Scc). Scc is a poor precursor of cysteine and sustains growth of a Cys-auxotrophic E. coli strain less efficiently than cysteine. However, at concentrations above 1 mM, Scc gave rise to suppression of the thymidine auxotrophy of strain β5520, while in the absence of thymidine no growth was detectable below 1 mM Scc. When β5419 cells bearing the thyA: Val146GUA allele on a high copy plasmid were plated on mineral glucose plates supplemented with Scc (3 mM), no colonies grew after prolonged incubation at 30° C. (The experiment was designed to detect a mutant at a frequency of $10^{-10}$.) To increase the mutation frequency, a mutS::spc+ (33) mutator allele was introduced in the genetic background of strain β5419 by P1 transduction, yielding strain β5432 (the mutS::spc+ disruption disables the mismatch repair system and leads to random transitions and frameshifts (34)). Colonies then appeared on the same medium with a frequency of about $10^{-8}$. No colonies were found on plates lacking Scc. A comparable frequency of Scc-suppressible clones was obtained after introduction by P1 transduction (33) of a dnaQ mutator allele (33) (to give strain β5435).

Abu misincorporation. The valine auxotroph CU505 (33) was grown in the presence of a limiting supply of valine and increasing concentrations of Abu (FIG. 3). The biomass of cells in cultures relative to the valine concentration in the medium did not change up to a 1 mM concentration of Abu. In contrast, when the valST222P allele was introduced into the chromosome (strain β5498), the yield of cells was diminished in the absence of Abu but increased up to 30% when Abu (0.2 mM) was added.

Thus, E. coli strains that proliferate only because of infiltration of the Val coding pathway were selected and all contained mutations leading to single amino acid substitutions in the editing site of ValRS. This observation is consistent with a central role for editing in restricting the genetic code to twenty amino acids, by preventing the invasion of other amino acids such as Abu. Indeed, the editing sites in IleRS and ValRS are rigorously conserved in even the most deeply branched organisms in the tree of life. However the translation accuracy maintained by editing may prevent further chemical diversification of proteins. Thus, disabling the editing function of a synthetase, as demonstrated in the present work, offers a a powerful approach to diversify the chemical composition of proteins produced in vivo.

For some synthetases, accuracy depends critically on an editing function at a site distinct from the aminoacylation site. Mutants of Escherichia coli that mischarge $tRiNA^{Val}$ with cysteine were sought by random mutagenesis of the whole chromosome. All mutations obtained were located in the editing site of valyl-tRNA synthetase. Over 20% of the valine in cellular proteins from such an editing mutant organism could be replaced with the noncanonical aminobutyrate, sterically similar to cysteine. Thus, the editing function may have played a central role in restricting the genetic code to twenty amino acids. Disabling this editing function offers a powerful new approach for diversifying the chemical composition of proteins and for emulating ambiguous evolutionary stages of translation.

Example 3

Correlation Between Yoxicity of α-aminobutyrate for E. coli Strains Harboring Different valS Alleles Mutated in the Editing Domain and Results of in vitro Editing Assays Carried Out with the Corresponding ValRS Enzyme Variants To investigate more deeply the editing phenotypes of the five aforementioned mutant ValRSs, and the relationship between cell viability and editing, plasmids harboring genes for mutant and wild-type ValRSs were constructed and placed under control of an arabinose-inducible promoter. These constructs were then used to investigate the in vivo phenotypes of the mutant enzymes. Separately, His-tagged versions of the mutant enzymes were constructed in parallel for use in purifying the enzymes for studies of aminoacylation and editing activities in vitro.

Construction of valS knockout strains: A 1.7 kb portion of the valS gene from pET16valS that contained the region encoding the editing domain of ValRS was excised using SalI and XhoI. This region was then replaced with a kanamycin marker (1.2 kb in size) liberated from pUC4K by flanking SalI restriction sites. Overhanging regions of the valS gene of 406 and 708 base pairs respectively were left to allow for homologous recombination (resulting plasmid named pLAN362). The kanamycin marker contained its own promoter and was inserted in the forward orientation with respect to the valS gene. To increase the amount of linearized product used for homologous recombination, the valS::kan from pLAN362 was PCR-amplified using primers annealing to the T7 promoter and terminator. The products of this reaction were visualized and purified in a 1% agarose TAE gel.

To get recombination into the E. coli chromosome, the linearized valS::kan was transformed by electroporation into a hyper recombinant strain of E. coli (JC8679, Stewart et al.) containing plasmid-borne valS from Haemophilus influenzae (pSU18valS). Recombinants were selected on Luria Broth agar plates supplemented with chloramphenicol (strain JC8679 is CmR) and low kanamycin (25 ug/ml) because efficiency of kanR markers can be decreased when it recombines into the chromosome, one recombinant chosen and named strain PS2838. PS2838 was infected with a P1 phage stock, phage were allowed to propagate for 3 hours then were stored in CHC13 at 4C. Transfer of genes and resistance markers was done by P1 phage transduction using standard protocols (Miller 1972) into MG1655 wild-type E. coli containing each of the valSpBAD constructs expressing either wild-type ValRS, T222P, R223H, D230N, V276A, and K277Q. Transductants were selected by plating on Luria Broth agar plates supplemented with kanamycin (25 ug/ml) and 0.2% arabinose, incubating at 25 C for 48 hours.

As expected transduction of the MG1655 strain alone did not yield colony growth. All transductants were restreaked onto media supplemented with 50 ug/ml kanamycin to ensure kanR and insertion of kanamycin marker into the E. coli chromosomal valS gene was verified by amplifying with a forward primer that annealed to a region on the chromosome just upstream of the valS gene (valS. 103) and a reverse primer annealing to the marker itself (puc4k.ol4). Transduction yielded the following strains of valS::kanR: wt ValRS-PS2847, T222P-PS2849, R223H-PS2862, D230N-PS2865, V276A-PS2851, K277Q-PS2853.

Plasmid Construction: A cautious approach was taken in this construction due to a lack of success introducing valS editing mutants previously. With this in mind initial constructs were done in a variation of pBAD18, a plasmid allowing for tight regulation of expression under control of an arabinose inducible promoter. Parent plasmid was a Histidine tagged valS construction received from Jack Horowitz which we verified by sequence analysis to done be pET16b (Novagen). Utilizing an internal restriction site and a restriction site located downstream of the valS gene in the multiple cloning site of pET16b, a large BamHI fragment was subcloned into pUC19 (pSCO2). In parallel, the parent plasmid was digested with SalI and BglII, restriction sites that flank the region of valS encoding the CP1, and this small segment was ligated into pUC19 (pSCO5).

The QuikChange mutagenesis kit (Stratagene, La Jolla, Calif.) was used on pSCO5 to introduce an A to C base change at nucleotide 663 to achieve the Thr to Pro substitution in residue 222 of ValRS. Both the wild-type and T222P SalI-BglII fragments were subcloned into pSCO2. The resulting vectors were digested with NcoI and SmaI to release fragments of the entire downstream region of valS which were then cloned into pVDC441, a variation of pBAD18 into which the upstream portion of valS from the pET16bvalS plasmid had been cloned using EcoRI and KpnI. The His tagged T222P construct was constructed by subcloning the mutated region of valS (DraIII/XhoI) from pVDC447 and ligating it into the pET16bvalS. The wild-type valS constructs, pBAD18valS and pET16bvalS, were eventually used as templates in the QuickChange mutagenesis protocol to generate mutations in valS corresponding to the mutants R223H, D230N, V276A, and K277Q. The entire valS gene for these vectors was then sequenced for each of these vectors to verify their integrity.

Mutant Toxicity Response to High Levels of α-Aminobutyrate: ΔvalS::kan+ strains expressing wild-type ValRS, T222P, R223H, D230N, V276A, and K277Q were each isolated on mineral standard medium (MS) (Richaud et al, 1993) supplemented with 0.2% glycerol, 0.02% arabinose and ampicillin(100 ug/mL). Single colonies from each strain were inoculated into liquid cultures of the same media composition and grown overnight to saturation. Cells were diluted in media 1:100 and a lawn of cells was spread and allowed to dry onto MS medium plates. α-aminobutyrate (50 uL of 0.1 M) was added to a central well created in each plate and plates were then incubated for 24 hours at 42 C. The relative response of each strain to high levels of noncognate α-aminobutyrate could then be evaluated based on diameter of toxicity halo observed.

Expression and Purification of ValRS Proteins: pET16b plasmids corresponding to the wild-type ValRS and each of the ValRS mutants were transformed into BL21 competent cells (Novagen). These cells were cultured in 250 mL of Luria Broth supplemented with ampicillin (100 ug/mL), when cells reached an optical density at 600nm of 1.0 expression of ValRS was induced with 1 mM IPTG for 5 hours. Cells were then stored at −80 C until purification. Cells were resuspended (50 mM $Na_2PO_4$, 300 mM NaCl, 50 mM B-ME, 30 mM Imidazole pH 7.4) and lysed 2×in French Press. Lysates were bound a Ni-NTA affinity column and eluted in lysis buffer with a gradient ranging from 30 mM to 250 mM Imidazole. Collected fractions were visualized on an 8% SDS-polyacyrlamide gel stained with coomassie brilliant blue to ensure purity, purest fractions were pooled and dialyzed into 25 mM Tris-HCl, 1 mM B-ME pH 7.5. Enzyme concentrations were determined by Bradford assay.

Aminoaclyation Assay, Misacylation, and Deacylation: Aminoacylation assays were performed at 37 C. in a 100 uL volume containing buffer (20 mM HEPES, 0.1 mM EDTA disodium salt, 0.15M $NH_4Cl$, 10 ug/mL BSA pH 7.5), 2 μM $MgCl_2$, 0.7 μM [$^3$H]Val, 20 μM cold Val, 2 μM $tRNA_{val}$ (Sigma) and 20 nM ValRS enzyme (adapted from Hendrickson et al. 2000). Aliquots (10 μL) of the reaction mixture were precipitated with tricholoracetic acid, and the level of aminoacylation of the tRNA was determined by scintillation counting.

Misacylation of Thr onto $tRNA_{val}$ was performed in the same conditions except 5.86 μM [$^3$H]Thr was substituted for Val in the reaction. To test deacylation rates for these enzymes it was necessary to generate [$^3$H]Thr-$tRNA_{val}$. This was done using ValRS with the T222P substitution purified previously (Doring et al, 2001), this enzyme was shown to form the [$^3$H]Thr-$tRNA_{val}$ complex. Enzyme was incubated with 2.5 μM $tRNA_{val}$ and 45 uM [$^3$H]Thr, incubated at 37 C. for 45 minutes, extracted twice in phenol:chloroform, and ethanol precipitated. Pellet was dissolved in 100 μL sterile $H_2O$ and scintillation counting was used to determine the success of the reaction. Deacylation reactions, done in triplicate for each enzyme, were performed in 155 mM Tris-HCl (pH 7.5), 100 μg/ml BSA, 10 mM MgCl2. At room temperature 2 nM enzyme was combined with [$^3$H]Thr-$tRNA_{val}$, at 3, 6, 9, 16, and 30 minutes aliquots (9 μL) of the reaction mixture were precipitated with tricholoracetic acid, and the amount of misaminoacylated [$^3$H]Thr-tRNA$_{val}$ remaining in the sample was determined by scintillation counting. A no enzyme control reaction was included to provide reference point.

When the percentage of Thr-tRNA$^{Val}$ hydrolyzed by each enzyme in deacylation assays in vitro was compared to the observed Abu-induced inhibition zone diameters in vivo, a pattern was clear (FIG. 5A). The T222P and K277Q ValRS mutant proteins have the most severe defects, for example, in deacylation of Thr tRNA$^{Val}$ in vitro (FIG. 5B) Strains bearing these mutations show a toxic response to only slightly raised levels of Abu in vivo. These two enzymes also accumulated high levels of mischarged Thr-tRNA$^{Val}$ in vitro. The D230N mutation appears to be less detrimental to the deacylase activity, exhibiting a slowed rate of deacylation. Similarly, toxicity in vivo was limited to intermediate levels of Abu. Having the V276A mutation appears to impart the least toxic response to exogenous Abu. This phenotype is reflected in a deacylation rate that is closer to wild-type ValRS than to that of the other mutant enzymes. Both D230N and V276A ValRS showed low levels of mischarging with respect to the other mutant enzymes as well. Thus, the ability of the mutant enzymes to hydrolyze in vitro misaminoacylated amino acids from tRNA$^{Val}$ correlated with the toxicity in vivo of exogenous noncognate amino acids that were added to cells bearing the same mutations in their ValRS.

Example 4

Construction of Strains of *E. coli* Expressing an Isoleucyl-tRNA Synthetase Mutated in the Editing Site Several studies have identified the editing domain of IleRS (Schmidt at Schimmel, 1004, Science), and more particularly the amino acids of the 239 to 250 region which are extremely conserved in the IleRS sequences of different organisms. Point mutations in this region generate enzymes partially or totally deficient in the editing function (Hendrickson, 2000). An artificial allele of the gene iles coding for isoleucyl-tRNA *E. coli* synthetase containing a succession fine residues replacing residues 239 to 250 has been constructed in the following manner: the pVDC433 (Hendrickson et al. 2001), derived from plasmid pBAD (Guzman et al., 1995) by insertion of the wild type ileS gene is digested by restriction enzymes ClaI and SpeI according to the instructions of the supplier, thus eliminating nucleotides 717 to 750 of the gene. The 5' phosphorylated oligonucleotides (Invitrogen Life Technologies): 5'pCTAGTAATCGCGGCGGCGGCGGCG-GCGGCGGCGGCGGCGGCGCGCGCAATAT (SEQ ID NO: 1) and5'pCGATATTGCGCGCGCCGCCGCCGCCG-CCGCCGCCGCCGCCGCGATTA (SEQ ID NO: 2) are hybridized and ligated with the plasmid pVDC433, previously cut by SlaI and SpeI under the following conditions: 0.3 pmoles of vector and 3 pmoles of each oligonucleotide are incubated for 10 minutes at 70 degrees C. after precipitation and resuspension in 10 ul of H$_2$O, after return to room temperature; the ligation is carried out using standard protocols. The ligation mixture is utilized to transform competent cells of the SureTM strain (Stratagene) by electroporation following the protocol of the supplier. The transformants are obtained and plasmid DNA prepared (Qiaprep Kit, Qiagen). The plasmid obtained in this manner, pTLH33, is sequenced and the insertion of 11 alanine codons is verified.

The pTLH33 plasmid is inserted in the wild type *E. coli* strain MG1655 to obtain strain PS2419. The allele obtained by deletion of the ileS gene, deltaileS203::kan, from strain IQ839 (Shiba and Schimmel, 1992) is introduced in strain PS2419 by P1 transduction according to a standard protocol (Miller, 1972), and a transducant, strain PS 2449, is obtained in rich medium supplemented with kanamycin (25 mg/L) and arabinose (0.02%). In the same way, strain PS2306 is constructed by insertion of the pVDC433 plasmid in strain MG1655 (resulting strain: PS2752) and P1 transduction of allele delta ileS203::kan in strain PS2752. Growth of the two strains deleted in the ileS locus, PS2306 and PS2449, requires the presence of arabinose, thus demonstrating the controlled expression of the wild type ileS gene (plasmid PVDC433, strain PS2306) and the mutated gene ileS ala11 (plasmid pTLH33, strain PS2449) respectively.

Example 5

Sensitivity of the Isoleucyl-tRNA Synthetase to Non Canonic Amino Acids

Strains PS2306 and PS2449 are tested for their sensitivity to artificial amino acids which present a steric resemblance to isoleucine. The cells are cultivated in MS mineral medium, succinate (0.2%), arabinose (0.2%) for 24 h at 37 degrees centigrade and diluted at 1/250in MS mineral medium. 0.5 ml of this cell suspension are spread on a Petri dish containing 25 ml of MS medium supplemented with succinate (0.2%) and arabinose (0.2%). A well is then prepared in the middle of the dish and filled with 0.1 ml of an amino acid solution:
1) 25 mM S-methyl cysteine
2) 25 mM homocysteine
3) 25 mM o-methyl-L-serine
4) 25 mM Norleucine
5) 25 mM Norvaline The Petri dishes are then incubated at 37 degrees centigrade for 24 hours and the appearance of a zone of inhibition around the well is recorded. The diameters of the zones of attenuated growth are measured as follows:

TABLE 3

| Amino acid | PS2306 | PS2449 |
| --- | --- | --- |
| S-methyl-L-cysteine | 1.3 cm | 3.0 cm |
| Homocysteine | 2.1 cm | 2.9 cm |
| O-methyl-L-serine | 2.2 cm | 5.6 cm |
| Norleucin | 2.9 cm | 3.4 cm |
| Norvaline | 3.7 cm | 8.0 cm |

All 5 non-canonic amino acids tested inhibit the growth of the two strains, but it is noted that in all cases there is a stronger inhibition on the strain expressing the mutated allele of the ileS gene in the editing site. Thus the mutated isoleucyl-tRNA synthetase seems to have an increased specificity for the substrate amino acid capable of loading tRNAile with non-natural amino acids.

Example 6

Biochemical Characterization of the IleRS239-250Ala mutant

Figure 4:
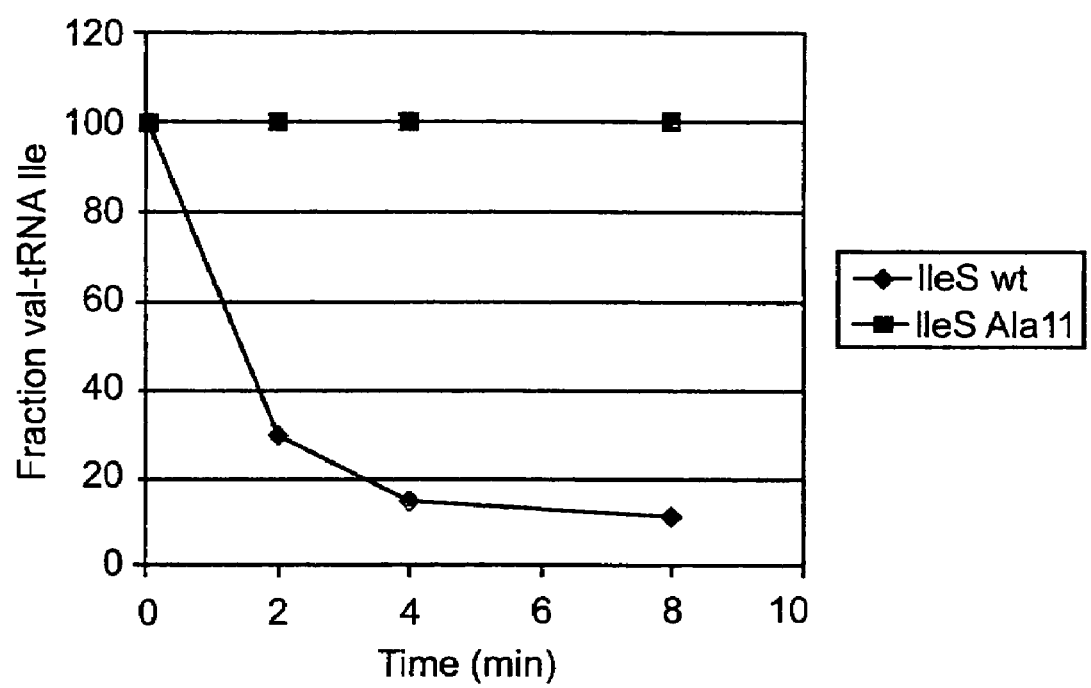
FIG. 4. A graph showing hydrolysis of valyl-tRNAile by wild type and mutated IleRS. This figure shows the large decrease of the editing activity of the mutant IleRS having 11 alanine residues in position aa 239-250 compared with the editing activity of the wild type IleRS. (square; ■): IleS ala 11

The wild type and mutant IleRS enzymes were purified from strains PS2306 and PS2449 by chromatography using the procedure described by Hendrickson et al. (2002). IletRNA loaced with the amino acid Val (Val-t-RNAIle) can be produced in large quantity by utilizing the editing mutant IleRS T242P (Hendrickson 2000). The utlization of this Val-tRNA/Ile has allowed testing of deacylation activity of several enzymes using the protocol described by Hendrickson, 2000. The results obtained, shown in FIG. 4, clearly show that the IleRS239-250 mutant is deficient in the deacylation function of Val-tRNAIle.

BIBLIOGRAPHY

1. U. L. RajBhandary, *J. Bacteriol.* 176, 547-52 (1994).
2. A. Böck, et al., *Mol. Microbiol.* 5, 515-20 (1991).
3. A. L. Weber, S. L. Miller, *J Mol. Evol.* 17, 273-84 (1981).
4. I. G. Fotheringham, N. Grinter, D. P. Pantaleone, R. F. Senkpeil, P. P. Taylor, *Biorg. Med. Chem.* 7, 2209-13 (1999).
5. M. Ibba, D. Söll, *Annu. Rev. Biochem.* 69, 617-50 (2000).
6. R. B. Loftfield, D. Vanderjagt, *Biochem. J.* 128, 1353-1356 (1972).
7. A. N. Baldwin, P. Berg, *J. Biol. Chem.* 241, 839-845 (1966).
8. E. W. Eldred, P. R. Schimmel, *J. Biol. Chem.* 247, 2961-4 (1972).
9. A. Fersht, in *Structure and mechanism in Protein Science*. (Freeman, New York, 1999) pp. 389-399.
10. K. Musier-Forsyth, P. J. Beuning, *Nat. Struct. Biol.* 7, 435-436 (2000).
11. H. Jakubowski, A. R. Fersht, *Nucleic Acids Res.* 9, 3105-17 (1981).
12. D. R. Liu, P. G. Schultz, *Proc. Natl. Acad. Sci. U.S.A.* 96, 4780-5 (1999).
13. M. Belfort, G. Maley, J. Pedersen-Lane, F. Maley, *Proc. Natl. Acad. Sci. U.S.A.* 80, 4914-8 (1983).
14. V. Döring, P. Marlière, *Genetics* 150, 543-51 (1998).
15. B. Lemeignan, P. Sonigo, P. Marlière, *J Mol. Biol.* 231, 161-6 (1993).
16. I. K. Dev, B. B. Yates, J. Leong, W. S. Dallas, *Proc. Natl. Acad. Sci. U.S.A* 85, 1472-6 (1988).
17. The 64 alleles of thyA with different codons at position 146 of the coding sequence were constructed as follows. First, a unique NheI site was introduced through a G429→A substitution in the thyA coding region by site-directed mutagenesis (24) of plasmid pTSO (14) to yield plasmid pTSO1. Oligonucleotides THY1 (5'- CTG-GATAAAATGGCGCTAGCACCGTGCCATGCATTC-3') (SEQ ID NO: 3) and THY2 (5'-TCTGCCACATA-GAACTGGAAGAATGCATGGCACGGT-3') (SEQ ID NO: 4) were used for this mutation which preserved the sense of the codon thus mutated. Plasmid pTSO1 was then digested with NheI and NsiI to remove from the thyA coding region an 18 bp fragment containing codon 146 (UGC). All 64 oligonucleotides of the thyA coding sequence from nucleotides 427 to 444 and the 64 oligonucleotides of the partial reverse sequence were constructed (GENAXIS. Biotechnology, Montigny le Bretonneux, France). The 64 pairs of complementary oligonucleotides were annealed and ligated with the digested plasmid pTSO 1.
18. Cysteine gradient plates were done as described in FIG. 1B legend. The effects of L-valine alone could not be directly examined because exogenous L-valine is known to inhibit growth of *E. coli* K12 in minimal medium (25). This inhibition is relieved if L-isoleucine is also supplied. Thus, the Ile-Val dipeptide was used as a valine source, because this dipeptide is transported across the cell membrane and then broken down to isoleucine and valine (26).
19. V. Döring, et al., Supplementary data can be found at the Science Web site.
20. M. J. Pine, *Antimicrobio. Agents Chemother.* 13, 676-85 (1978).
21. *E. coli* chromosomal DNA was extracted using a DNeasy Tissue Kit (Qiagen GmbH, Hilden, Germany) following the instructions of the manufacturer. PCR to amplify the valS gene was performed as follows: denaturation at 94° C. for 3 min, followed by 30 cycles of 30 sec at 94° C., annealing at 57° C. for 30 s, and primer extension at 72° C. for 200 sec. The final step was a primer extension at 72° C. for 600 sec. The reaction was carried out using 2 units of Vent DNA polymerase (New England Biolabs, Beverly, Mass.) and 100 ng of chromosomal DNA in a 100 µl reaction mixture. The following primers were used: VAL1 (5'-GGGGAATTCGGTGTGTGAAATTGCCGCA-GAACG-3')(SEQ ID NO: 5), and VAL2 (5'-GGCAAGCTTTCAGGTATTTGCTGCCCAGATCGA-3')(SEQ. ID NO: 6) Two independent PCR amplification products of each mutant were sequenced (GENAXIS Biotechnology, Montigny le Bretonneux, France).
22. L. Lin, S. P. Hale, P. Schimrnel, *Nature* 384, 33-4 (1996).
23. O. Nureki, et al., *Science* 280, 578-82 (1998).
24. M. Ansaldi, M. Lepelletier, V. Mejean, *Anal. Biocheni.* 234, 110-1 (1996).
25. M. De Felice, et al., *J. Mol. Biol.* 156, 1-7 (1977).
26. A. J. Sussman, C. Gilvarg, *Annu. Rev. Biochem.* 40, 397-408 (1971).
27. C. Richaud, et al., *J. Biol. Chem.* 268, 26827-35 (1993).
28. E. Schmidt, P. Schimmel, *Biochemistry* 34, 11204-10 (1995).
29. L. Lin, P. Schimmel, *Biochemistry* 35, 5596-601 (1996).
30. L. M. Guzman, D. Belin, M. J. Carson, J. Beckwith, *J. Bacteriol.* 177, 4121-30 (1995).
31. T. L. Hendrickson, T. K. Nomanbhoy, P. Schimmel, *Biochemistry* 39, 8180-8186 (2000).
32. K. Gevaert, J. Vandekerckhove, *Electrophoresis* 21, 1145-54 (2000).
33. mutS::spc+ allele (gift of F. Taddei, Hôpital Necker-Enfants, Paris); ΔnrdD::kan+ allele, laboratory collection; ΔdnaQ::tet allele (gift of J. Shapiro, University of Chicago, IL); CU505 (Δ(ilvE-ilvC)2049 leu455 galT1 IN(rrnD-rrnE)1) gift of Dr. M. Berlyn from the *E. coli* Genetic Stock Center (New Haven, Conn.). Transfer of genes and of resistance markers by P1 transduction were carried out using standard protocols (35).
34. P. Modrich, *Annu. Rev. Genet.* 25, 229-53 (1991).
35. J. H. Miller, *Experiments in Molecular Genetics* (Cold Spring Harbor Laboratory Press, Cold Spring Harbor, N.Y., 1972).
36. Guzman, L. M., Belin, D., Carson, M. J., and Beckwith, J. (1995). Tight regulation, modulation, and high-level expression by vectors containing the arabinose PBAD promoter. J. Bacteriol. 177, 4121-4130
37. Hendrickson, T. L., Nomanbhoy, T. K., and Schimmel, P. (2000). Errors from selective disruption of the editing center in a tRNA synthetase. Biochemistry 39, 8180-8186
38. Hendrickson, T. L., Nomanbhoy, T. K., de Crecy-Lagard, V., Fukai, S., Nureki, O., Yokoyama, S., and Schimmel, P. (2002). Mutational separation of two pathways for editing by a class I tRNA synthetase. Mol. Cell 9, 353-362
39. Schmidt, E., and Schimmel, P. (1994). Mutational isolation of a sieve for editing in a transfer RNA synthetase. Science 264, 265-267
40. Shiba, K., and Schimmel, P. (1992). Functional assembly of a randomly cleaved protein. Proc. Natl. Acad. Sci. USA 89, 9964-9968

We claim:

1. A method for mischarging an isoleucyl tRNA with a noncognate amino acid using an isoleucyl tRNA synthetase variant comprising contacting said noncognate amino acid and said isoleucyl tRNA with an isoleucyl tRNA synthetase variant of wild type isoleucyl tRNA synthetase (IleRS) from *E. coli*, wherein residues 240 to 250 (SEQ ID NO: 20) in the editing domain of said isoleucyl tRNA synthetase variant are replaced by a succession of alanine residues compared to said wild type isoleucyl tRNA synthetase.

2. A method according to claim 1, wherein said noncognate amino acid is a noncanonical amino acid.

3. A method for producing in vivo proteins comprising at least one noncanonical amino acid comprising:
   a) selecting a cell strain comprising an isoleucyl tRNA synthetase variant of wild type isoleucyl tRNA synthetase (IleRS) from *E. Coli*, wherein residues 240 to 250 (SEQ ID NO: 20) in the editing domain of the isoleticyl tRNA synthetase variant have been replaced by a succession of alanine residues compared to said wild type isoleucyl tRNA synthetase, allowing the isoleucyl tRNA synthetase variant to mischarge an isoleucyl tRNA with said at least one noncanonical amino acid;
   b) culturing the selected strain in a culture medium comprising said noncanonical amino acid, or one of its precursors, under conditions favorable for the growth of said strain; and
   c) recovering from the culture medium or from the cells obtained in step b) the proteins containing said noncanonical amino acid.

4. The method according to claim 1 or 3, wherein the isoleucyl tRNA synthetase variant is capable of mischarging the isoleucyl tRNA with a canonical amino acid sterically similar to the amino acid charged by the wild type isoleticyl tRNA synthetase.

5. The method according to one of claims 1-3, wherein the isoleucyl tRNA synthetase variant is capable of mischarging the isoleucyl tRNA with a noncanonical amino acid sterically similar to the amino acid charged by the wild type isoleucyl tRNA synthetase on the isoleucyl tRNA.

6. A method for obtaining cells capable of producing in vivo proteins comprising at least one noncanonical amino acid, comprising the steps of:
   a) assaying cells comprising an isoleucyl tRNA synthetase variant of wild type isoleucyl tRNA synthetase (IleRS) from *E. Coli*, said variant having residues 240 to 250 (SEQ ID NO: 20) in its editing domain replaced by a succession of alanine residues, for the ability to mischarge an isoleucyl tRNA with a noncanonical amino acid; and
   b) identifying, selecting and/or cloning cells which comprise said isoleucyl tRNA synthetase variant and which have the ability to mischarge a noncanonical amino acid.

7. A method according to any one of claims 3 and 6, wherein the noncanonical amino acid is an unnatural amino acid.

8. The method of any one of claims 3 and 6, wherein the cells are microbial or animal cells.

9. The method of claim 8, wherein said microbial cells are bacteria, yeast or fungi.

10. The method of claim 9, wherein said bacteria are *Escherichia coli* or *Acinetobacter*.

11. The method of any one of claims 1-3 and 6, wherein the replacement of the editing domain of the isoleucyl tRNA synthetase variant is obtained by homologous recombination.

12. The method of claim 11, wherein the replacement of the editing domain of the isoleucyl tRNA synthetase variant is obtained by using an allelic replacement vector.

13. A method according to claim 2 wherein said noncanonical amino acid is selected from S-methyl-L-cysteine, homocysteine, O-methyl-L-serine, norleucine and norvaline.

14. The method according to claim 3, wherein the noncanonical amino acid is selected from S-methyl-L-cysteine, homocysteine, O-methyl-L-serine, norleucine and norvaline.

* * * * *

SEQUENCE LISTING

<160> NUMBER OF SEQ ID NOS: 20

<210> SEQ ID NO 1
<211> LENGTH: 52
<212> TYPE: DNA
<213> ORGANISM: artificial
<220> FEATURE:
<221> NAME/KEY: primer_bind
<222> LOCATION: (1)..(52)
<223> OTHER INFORMATION: 5' phosphorylated oligonucleotide for
      introducing mutation in the editing domain of isoleucyl-tRNA
      synthetase gene Ile RS

<400> SEQUENCE: 1
ctagtaatcg cggcggcggc ggcggcggcg gcggcggcgg cgcgcgcaat at           52

<210> SEQ ID NO 2
<211> LENGTH: 50
<212> TYPE: DNA
<213> ORGANISM: artificial
<220> FEATURE:
<221> NAME/KEY: misc_binding
<222> LOCATION: (1)..(50)
<223> OTHER INFORMATION: 5' phosphorylated oligonucleotide for
      introducing mutation in the editing domain of isoleucyl-tRNA
      synthetase gene Ile RS

<400> SEQUENCE: 2
cgatattgcg cgcgccgccg ccgccgccgc cgccgccgcc gccgcgatta              50

<210> SEQ ID NO 3
<211> LENGTH: 36
<212> TYPE: DNA
<213> ORGANISM: artificial
<220> FEATURE:
<221> NAME/KEY: misc_binding
<222> LOCATION: (1)..(36)
<223> OTHER INFORMATION: 5' phosphorylated oligonucleotide for
      introducing mutation in the thyA gene

<400> SEQUENCE: 3
ctggataaaa tggcgctagc accgtgccat gcattc                            36

<210> SEQ ID NO 4
<211> LENGTH: 36
<212> TYPE: DNA
<213> ORGANISM: artificial
<220> FEATURE:
<221> NAME/KEY: misc_binding
<222> LOCATION: (1)..(33)
<223> OTHER INFORMATION: 5' phosphorylated oligonucleotide for
      introducing mutation in thyA gene

<400> SEQUENCE: 4
tctgccacat agaactggaa gaatgcatgg cacggt                            36

<210> SEQ ID NO 5
<211> LENGTH: 33
<212> TYPE: DNA
<213> ORGANISM: artificial
<220> FEATURE:
<221> NAME/KEY: misc_binding
<222> LOCATION: (1)..(33)
<223> OTHER INFORMATION: 5' phosphorylated PCR oligonucleotide to
      amplify valS gene

<400> SEQUENCE: 5

```
ggggaattcg gtgtgtgaaa ttgccgcaga acg                              33
```

<210> SEQ ID NO 6
<211> LENGTH: 33
<212> TYPE: DNA
<213> ORGANISM: artificial
<220> FEATURE:
<221> NAME/KEY: misc_binding
<222> LOCATION: (1)..(33)
<223> OTHER INFORMATION: 5' phosphorylated PCR oligonucleotide to
      amplify valS gene

<400> SEQUENCE: 6

```
ggcaagcttt caggtatttg ctgcccagat cga                              33
```

<210> SEQ ID NO 7
<211> LENGTH: 13
<212> TYPE: PRT
<213> ORGANISM: Escherichia coli
<220> FEATURE:
<221> NAME/KEY: misc_feature
<223> OTHER INFORMATION: IleRS protein fragment

<400> SEQUENCE: 7

Trp Thr Thr Thr Pro Trp Thr Leu Pro Ala Asn Arg Ala
1               5                   10

<210> SEQ ID NO 8
<211> LENGTH: 16
<212> TYPE: PRT
<213> ORGANISM: Escherichia coli
<220> FEATURE:
<221> NAME/KEY: misc_feature
<223> OTHER INFORMATION: IleRS protein fragment

<400> SEQUENCE: 8

Gly Thr Gly Ala Val His Thr Ala Pro Gly His Gly Pro Asp Asp Tyr
1               5                   10                  15

<210> SEQ ID NO 9
<211> LENGTH: 13
<212> TYPE: PRT
<213> ORGANISM: Saccharomyces cerevisiae
<220> FEATURE:
<221> NAME/KEY: misc_feature
<223> OTHER INFORMATION: IleRS protein fragment

<400> SEQUENCE: 9

Trp Thr Thr Thr Pro Trp Thr Leu Pro Ser Asn Leu Ser
1               5                   10

<210> SEQ ID NO 10
<211> LENGTH: 16
<212> TYPE: PRT
<213> ORGANISM: Saccharomyces cerevisiae
<220> FEATURE:
<221> NAME/KEY: misc_feature
<223> OTHER INFORMATION: IleRS protein fragment

<400> SEQUENCE: 10

Gly Thr Gly Ile Val His Asn Ala Pro Ala Phe Gly Glu Glu Asp Asn
1               5                   10                  15

<210> SEQ ID NO 11
<211> LENGTH: 13
<212> TYPE: PRT
<213> ORGANISM: Homo sapiens
<220> FEATURE:

```
<221> NAME/KEY: misc_feature
<223> OTHER INFORMATION: IleRS protein fragment

<400> SEQUENCE: 11

Trp Thr Thr Thr Pro Trp Thr Leu Pro Ser Asn Leu Ala
1               5                   10

<210> SEQ ID NO 12
<211> LENGTH: 16
<212> TYPE: PRT
<213> ORGANISM: Homo sapiens
<220> FEATURE:
<221> NAME/KEY: misc_feature
<223> OTHER INFORMATION: IleRS protein fragment

<400> SEQUENCE: 12

Gly Thr Gly Val Val His Gln Ala Pro Tyr Phe Gly Ala Glu Asp Tyr
1               5                   10                  15

<210> SEQ ID NO 13
<211> LENGTH: 13
<212> TYPE: PRT
<213> ORGANISM: Escherichia coli
<220> FEATURE:
<221> NAME/KEY: misc_feature
<223> OTHER INFORMATION: ValRS protein fragment

<400> SEQUENCE: 13

Ala Thr Thr Arg Pro Glu Thr Leu Leu Gly Asp Thr Gly
1               5                   10

<210> SEQ ID NO 14
<211> LENGTH: 16
<212> TYPE: PRT
<213> ORGANISM: Escherichia coli
<220> FEATURE:
<221> NAME/KEY: misc_feature
<223> OTHER INFORMATION: ValRS protein fragment

<400> SEQUENCE: 14

Gly Thr Gly Cys Val Lys Ile Thr Pro Ala His Asp Phe Asn Asp Tyr
1               5                   10                  15

<210> SEQ ID NO 15
<211> LENGTH: 13
<212> TYPE: PRT
<213> ORGANISM: Saccharomyces cerevisiae
<220> FEATURE:
<221> NAME/KEY: misc_feature
<223> OTHER INFORMATION: ValRS protein fragment

<400> SEQUENCE: 15

Ala Thr Thr Arg Pro Glu Thr Ile Phe Gly Asp Thr Ala
1               5                   10

<210> SEQ ID NO 16
<211> LENGTH: 16
<212> TYPE: PRT
<213> ORGANISM: Saccharomyces cerevisiae
<220> FEATURE:
<221> NAME/KEY: misc_feature
<223> OTHER INFORMATION: ValRS protein fragment

<400> SEQUENCE: 16

Gly Thr Gly Ala Val Lys Ile Thr Pro Ala His Asp Gln Asn Asp Tyr
1               5                   10                  15
```

-continued

```
<210> SEQ ID NO 17
<211> LENGTH: 13
<212> TYPE: PRT
<213> ORGANISM: Homo sapiens
<220> FEATURE:
<221> NAME/KEY: misc_feature
<223> OTHER INFORMATION: ValRS protein fragment

<400> SEQUENCE: 17

Ala Thr Thr Arg Ile Glu Thr Met Leu Gly Asp Val Ala
1               5                   10

<210> SEQ ID NO 18
<211> LENGTH: 16
<212> TYPE: PRT
<213> ORGANISM: Homo sapiens

<400> SEQUENCE: 18

Gly Thr Gly Ala Val Lys Ile Thr Pro Ala His Asp Gln Asn Asp Tyr
1               5                   10                  15

<210> SEQ ID NO 19
<211> LENGTH: 17
<212> TYPE: PRT
<213> ORGANISM: artificial
<220> FEATURE:
<221> NAME/KEY: misc_feature
<223> OTHER INFORMATION: AlaXp yeast protein fragment (Lys156-Arg172
      swissprot:p53960)

<400> SEQUENCE: 19

Lys Pro Val Leu Glu Pro Ser Asp Tyr Phe Asn Tyr Ile Glu Leu Asn Arg
1               5                   10                  15

<210> SEQ ID NO 20
<211> LENGTH: 11
<212> TYPE: PRT
<213> ORGANISM: Escherichia coli
<220> FEATURE:
<221> NAME/KEY: misc_feature
<223> OTHER INFORMATION: IleRS protein fragment

<400> SEQUENCE: 20

Trp Thr Thr Thr Pro Trp Thr Leu Pro Ala Asn
1               5                   10
```